(12) United States Patent
Daly

(10) Patent No.: US 11,724,984 B2
(45) Date of Patent: Aug. 15, 2023

(54) CARBONDISULFIDE DERIVED ZWITTERIONS

(71) Applicant: Thomas Daly, Arlington Heights, IL (US)

(72) Inventor: Thomas Daly, Arlington Heights, IL (US)

(*) Notice: Subject to any disclaimer, the term of this patent is extended or adjusted under 35 U.S.C. 154(b) by 281 days.

(21) Appl. No.: 17/088,615

(22) Filed: Nov. 4, 2020

(65) Prior Publication Data

US 2022/0135525 A1     May 5, 2022

(51) Int. Cl.
*C07C 329/14*     (2006.01)
*C07C 333/14*     (2006.01)

(52) U.S. Cl.
CPC .......... *C07C 329/14* (2013.01); *C07C 333/14* (2013.01)

(58) Field of Classification Search
None
See application file for complete search history.

(56) References Cited

PUBLICATIONS

Nikolovski et al. (Vestnik Slovenskega Kemijskega Drustva / Vestn. Slov. Kern. Drus., 1986, vol. 33, Issue: Suppl., "The UV spectra of some dithiocarbamates", p. 177-178). (Year: 1986).*

* cited by examiner

*Primary Examiner* — Sudhakar Katakam
*Assistant Examiner* — Jennifer C Sawyer
(74) *Attorney, Agent, or Firm* — Clifford H. Kraft

(57) ABSTRACT

Amines and amine derivatives that improve the buffering range, and/or reduce the chelation and other negative interactions of the buffer and the system to be buffered. The reaction of amines or polyamines with various molecules to form polyamines with differing pKa's will extend the buffering range, derivatives that result in polyamines that have the same pKa yields a greater buffering capacity. Derivatives that result in zwitterionic buffers improve yield by allowing a greater range of stability.

5 Claims, 32 Drawing Sheets

A, D and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. G is chosen from -H, -CH3, -CH2CH3, -OH. J is chosen from alkyl, alkenyl, alkynyl, branched or linear, -H, -(CH2CH2O)$_n$H, -(CH2CH2CH2O)$_n$H, -(CH2CH(CH3)O)$_n$H, -(CH2C(CH3)2O)$_n$H. L, M, and Q are chosen from N or C. n is an integer greater than zero, m is 1 or 2.

A, D and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. G is chosen from -H, -CH3, -CH2CH3, -OH. J is chosen from alkyl, alkenyl, alkynyl, branched or linear, -H, -(CH2CH2O)$_n$H, -(CH2CH2CH2O)$_n$H, -(CH2CH(CH3)O)$_n$H, -(CH2C(CH3)2O)$_n$H. L, M, and Q are chosen from N or C. n is an integer greater than zero.

A, D and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. G is chosen from -H, -CH3, -CH2CH3, -OH. J is chosen from alkyl, alkenyl, alkynyl, branched or linear, -H, -(CH2CH2O)nH, -(CH2CH2CH2O)nH, -(CH2CH(CH3)O)nH, -(CH2C(CH3)2O)nH. L, M, and Q are chosen from N or C. n is an integer greater than zero.

G is chosen from -H, -CH3, -CH2CH3, -OH. J is chosen from alkyl, alkenyl, alkynyl, branched or linear, -H, -(CH2CH2O)nH, -(CH2CH2CH2O)nH, -(CH2CH(CH3)O)nH, -(CH2C(CH3)2O)nH. L, M, and Q are chosen from N or C. n is an integer greater than zero.

A, A', D, D' and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. m is an integer, zero or greater.

A, D, and E are independantly chosen from, -H, -OH, -CH3, -CH2CH3, -CH2OH. G is chosen from -H, -CH3, -CH2CH3, -OH. n is an integer greeater than 0. R is -H, -CH3, or -CH2CH3. J is chosen from alkyl, alkenyl, alkynyl, branched or linear, -H, -(CH$_2$CH$_2$O)$_n$H, -(CH$_2$CH$_2$CH$_2$O)$_n$H, -(CH$_2$CH(CH$_3$)O)$_n$H, -(CH$_2$C(CH$_3$)$_2$O)$_n$H.

L, M, and Q are chosen from N or C.

Figure 11

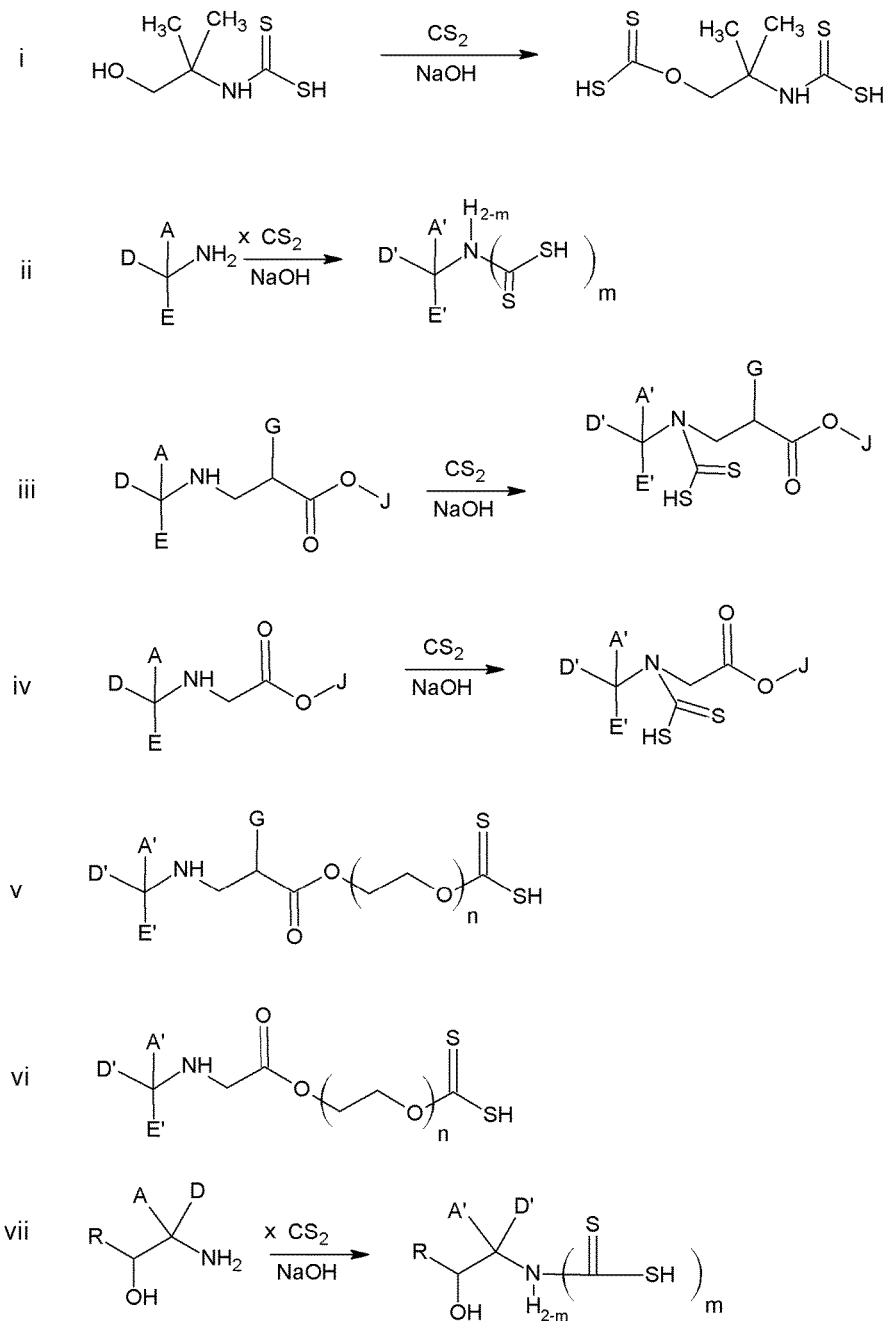

A,A', D,D', E and E' are independantly chosen from -H, -CH3, -CH2CH3, -CH2CH2CH3, -CH2OH, -CH2OCS2H, -CH2COOH, -CH2CH2COOH, -CH2CH(CH3)COOH, -CH2PO(OH)2. G is chosen from -H, -CH3, -CH2CH3, -OH. R is chosen from alkyl, alkenyl, alkynyl, branched or linear from 1 to 22 carbons. J is chosen from alkyl, alkenyl, alkynyl, branched or linear, -H, -(CH2CH2O)nH, -(CH2CH2CH2O)nH, -(CH2CH(CH3)O)nH, -(CH2C(CH3)2O)nH. L, M, and Q are chosen from N or C. n is an integer greater than zero, m is 1 or 2 and x is the sum of m and the number of hydroxyl groups in A,D, and E.

A, D and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. G is chosen from -H, -CH3, -CH2CH3, -OH. J is chosen from alkyl, alkenyl, alkynyl, branched or linear, -H, -(CH2CH2O)nH, -(CH2CH2CH2O)nH, -(CH2CH(CH3)O)nH, -(CH2C(CH3)2O)nH. L and L' are independantly chosen from -H, Alkyl, linear or branched, saturated or unsaturated from 1 to 22 carbons.

A, A', D, D', E and E' are independantly chosen from -H, -CH3, -CH2CH3, -CH2CH2CH3, -CH2OH, -CH2COOH, -CH2CH2COOH, -CH2CH(CH3)COOH, -CH2PO(OH)2. L, L', M, M', Q, and Q' are chosen from N or C such that 0 or 1 of L, M, anQ are N, and 1 or 0 of L',M', and Q', are N.

A, D and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. G is chosen from -H, -CH$_3$, -CH$_2$CH$_3$, -OH. J is chosen from alkyl, alkenyl, alkynl, branched or linear, -H, -CH$_3$, -CH$_2$CH$_3$, -OH, -CH$_2$OH, L, M, and Q are chosen from N or C. n is an integer greater than zero.

A, D and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. G is chosen from -H, -CH$_3$, -CH$_2$CH$_3$, -OH. J is chosen from alkyl, alkenyl, alkynl, branched or linear, -H, -CH$_3$, -CH$_2$CH$_3$, -OH, -CH$_2$OH, L, M, and Q are chosen from N or C. n is an integer greater than one, m is an iteger.

A, D and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. G is chosen from -H, -CH3, -CH2CH3, -OH. J is chosen from alkyl, alkenyl, alkynyl, branched or linear, -H, -(CH2CH2O)nH, -(CH2CH2CH2O)nH, -(CH2CH(CH3)O)nH, -(CH2C(CH3)2O)nH. L and L' are independantly chosen from -H, Alkyl, linear or branched, saturated or unsaturated from 1 to 22 carbons.

A and D are independantly chosen from -H, -CH3, -CH2CH3, -CH2CH2CH3, -CH2OH, -CH(OH)R, -CH$_2$COOH, -CH$_2$CH$_2$COOH, -CH$_2$CH(CH$_3$)COOH, -CH$_2$PO(OH)$_2$. R is alkyl, saturated or unsaturated, linear or branched, n is an integer 0 or greater.

Figure 20

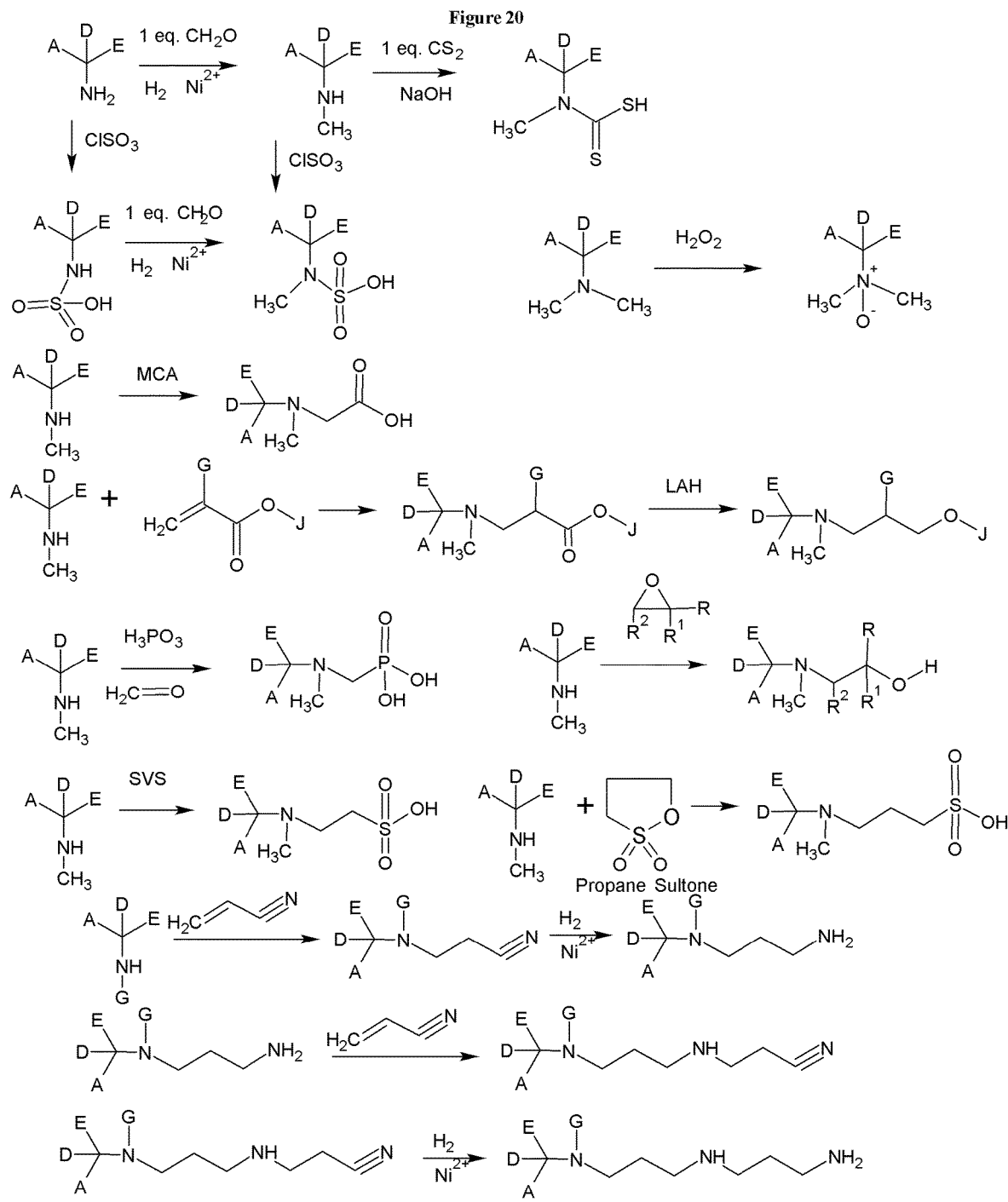

A,D and E are independantly chosen from -H, -CH3, -CH2CH3, -CH2CH2CH3, -CH2OH, -CH(OH)R, -CH$_2$COOH, -CH$_2$CH$_2$COOH, -CH$_2$CH(CH$_3$)COOH, -CH$_2$PO(OH)$_2$. n and m are an integers 0 or greater. G is chosen from -H, -CH3, -CH2CH3, -OH. J is chosen from alkyl, alkenyl, alkynyl, branched or linear, -H, -(CH$_2$CH$_2$O)$_n$H, -(CH$_2$CH$_2$CH$_2$O)$_n$H, -(CH$_2$CH(CH$_3$)O)$_n$H, -(CH$_2$C(CH$_3$)$_2$O)$_n$H. R, R1 and R2 are independently chosen from -H, alkyl, linear or branched, -(CH2)$_m$COOH A, G, and E, is chosen from N or C. R, R¹ and J are independently chosen from alkyl, saturated or unsaturated, branched or linear, from 1 to 22 carbons, -H, -CH$_2$OH, -CH$_2$CH$_2$OH, -C(Q)(Q')(Q") where Q,Q', and Q" are independently chosen from -H, -CH$_3$, -CH$_2$CH$_3$, -CH$_2$OH, L is chosen from -H, -CH3, -CH2CH3, -OH. L is chosen from -H, -CH$_3$, -CH$_2$CH$_3$, -CH$_2$OH. n' is the standard repeating unit of a polymer, dimer or oligamer.

A, G, and E, is chosen from N or C, such that only one may be N, the remainder C. J is chosen from alkyl, saturated or unsaturated, branched or linear, from 1 to 22 carbons, -H, -CH$_2$OH, -CH$_2$CH$_2$OH, -C(Q)(Q')(Q") where Q,Q', and Q" are independently chosen from -H, -CH$_3$, -CH$_2$CH$_3$, -CH$_2$OH, L is chosen from -H, -CH$_3$, -CH$_2$CH$_3$, -CH$_2$OH. n' is the standard repeating unit of a polymer, dimer or oligamer.

Figure 23

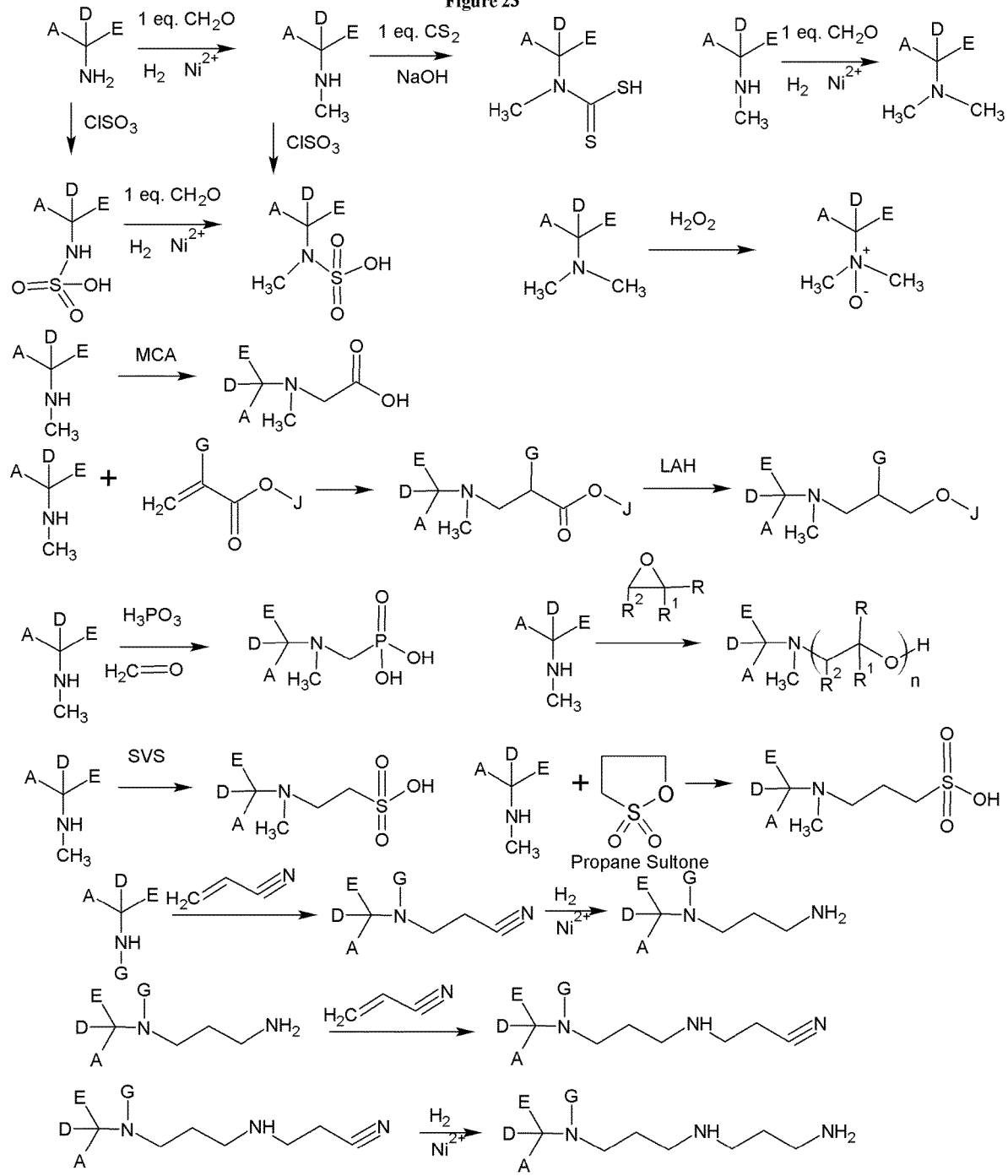

A, D and E are independantly chosen from -H, alkyl, saturated or unsaturated, linear or branched from $C_8$ to $C_{22}$. n and m are an integers 0 or greater. G is chosen from -H, -CH3, -CH2CH3, -OH. J is chosen from alkyl, alkenyl, alkynyl, branched or linear, -H, -(CH$_2$CH$_2$O)$_n$H, -(CH$_2$CH$_2$CH$_2$O)$_n$H, -(CH$_2$CH(CH$_3$)O)$_n$H, -(CH$_2$C(CH$_3$)$_2$O)$_n$H. R, R1 and R2 are independently chosen from -H, alkyl, linear or branched, -(CH2)$_m$COOH

Figure 24

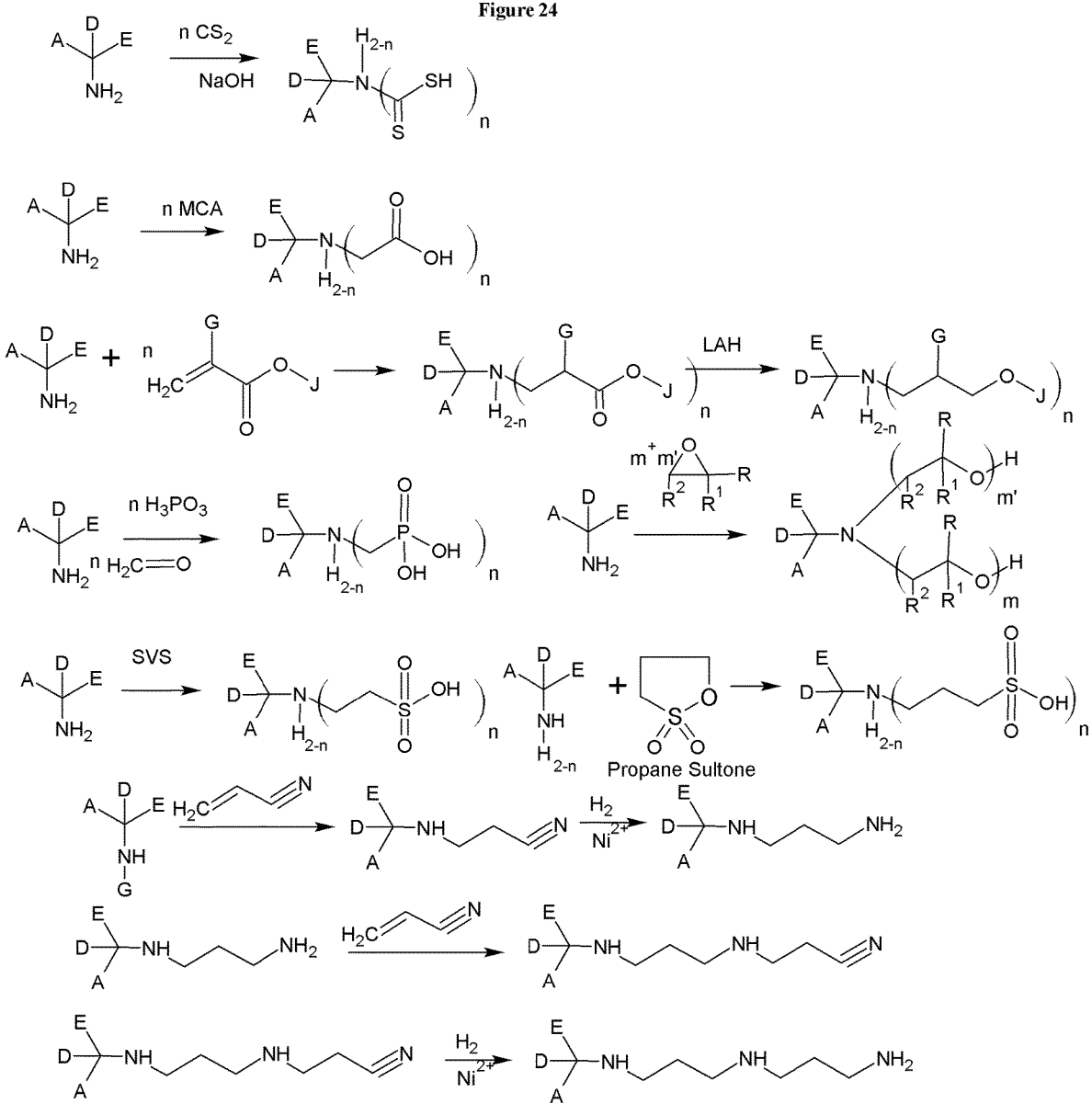

A,D and E are independantly chosen from -H, alkyl, saturated or unsaturated, linear or branched from $C_8$ to $C_{22}$. n, m and m' are integers 0 or greater. G is chosen from -H, -CH3, -CH2CH3, -OH. J is chosen from alkyl, alkenyl, alkynyl, branched or linear, -H, -(CH$_2$CH$_2$O)$_n$H, -(CH$_2$CH$_2$CH$_2$0)$_n$H, -(CH$_2$CH(CH$_3$)O)$_n$H, -(CH$_2$C(CH$_3$)$_2$O)$_n$H. R, R1 and R2 are independently chosen from -H, alkyl, linear or branched, -(CH2)$_m$COOH

Figure 25

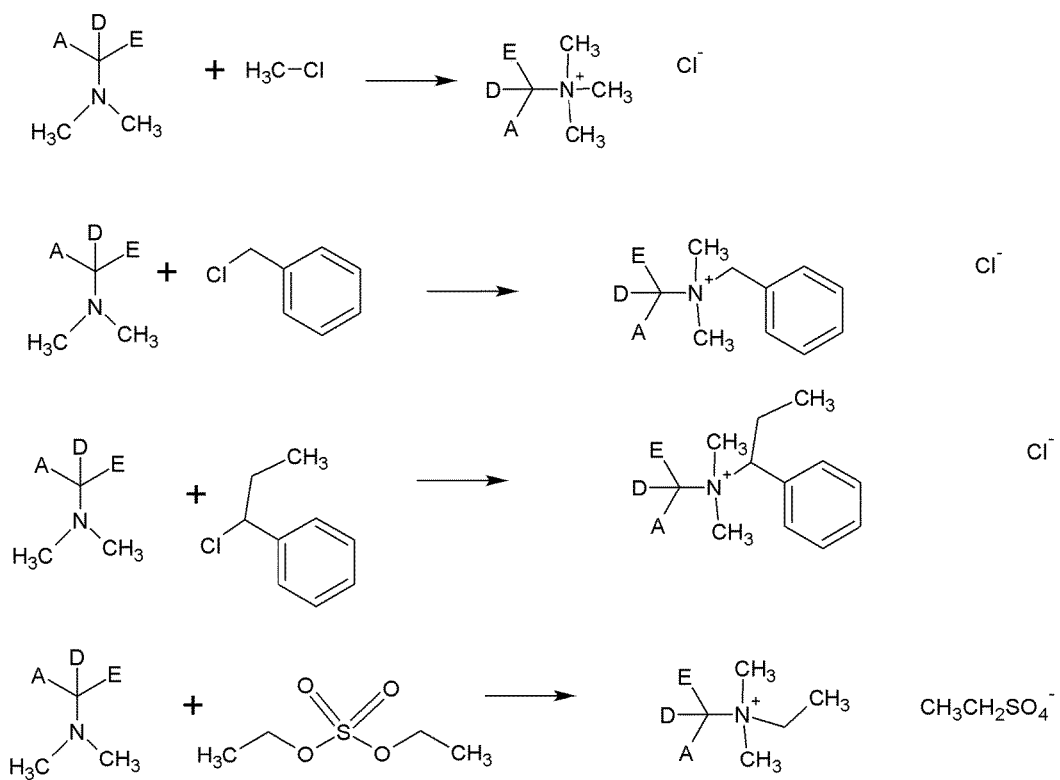

A,D and E are independantly chosen from -H, alkyl, saturated or unsaturated, linear or branched from $C_8$ to $C_{22}$. n and m are an integers 0 or greater. G is chosen from -H, -CH3, -CH2CH3, -OH. J is chosen from alkyl, alkenyl, alkynyl, branched or linear, -H, -(CH$_2$CH$_2$O)$_n$H, -(CH$_2$CH$_2$CH$_2$O)$_n$H, -(CH$_2$CH(CH$_3$)O)$_n$H, -(CH$_2$C(CH$_3$)$_2$O)$_n$H. R, R1 and R2 are independently chosen from -H, alkyl, linear or branched, -(CH2)$_m$COOH

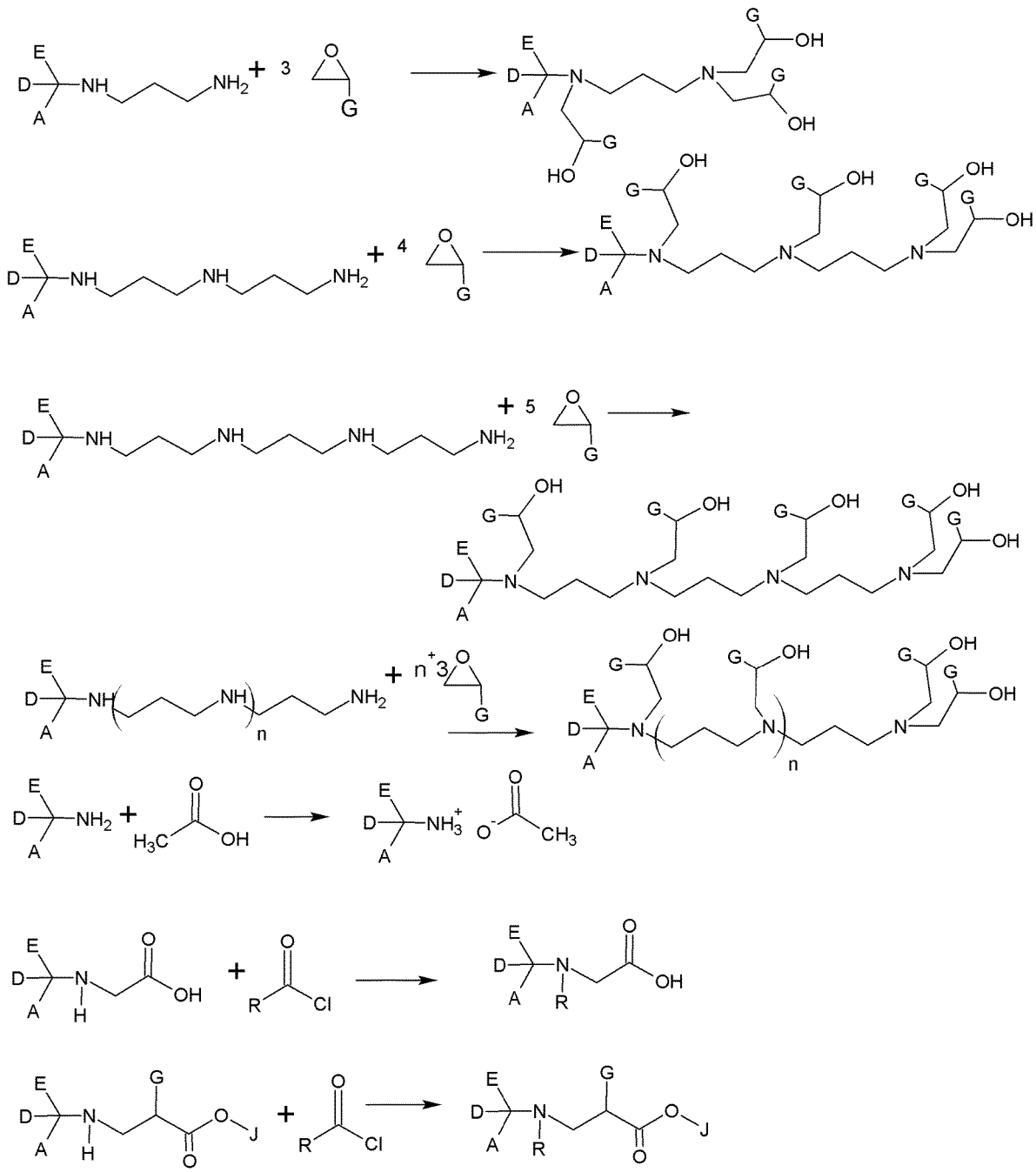

Figure 26

A,D and E are independantly chosen from -H, alkyl, saturated or unsaturated, linear or branched from $C_8$ to $C_{22}$. G is chosen from -H, -$CH_3$, -$CH_2CH_3$, -OH. J is chosen from alkyl, alkenyl, alkynyl, branched or linear, saturated or unsaturated, cyclic or acyclic from 1 to 22 carbons, -H, -$(CH_2CH_2O)_nH$, -$(CH_2CH_2CH_2O)_nH$, -$(CH_2CH(CH_3)O)_nH$, -$(CH_2C(CH_3)_2O)_nH$. R is chosen from alkyl, alkenyl, alkynyl, branched or linear, saturated or unsaturated, cyclic or acyclic from 1 to 22 carbons. n is an integer 1 or greater.

A and D are independantly chosen from -H, -CH3, -CH2CH3, -CH2CH2CH3, -CH2OH, -CH$_2$COOH, -CH$_2$CH$_2$COOH, -CH$_2$CH(CH$_3$)COOH, -CH$_2$PO(OH)$_2$. n is 1 or 2. R and R1 are alkyl, saturated or unsaturated, linear or branched, cyclic or acyclic from 1 to 22 carbons.

A and D are independantly chosen from -H, -CH3, -CH2CH3, -CH2CH2CH3, -CH2OH, -CH$_2$COOH, -CH$_2$CH$_2$COOH, -CH$_2$CH(CH$_3$)COOH, -CH$_2$PO(OH)$_2$. n is 1 or 2. R and R1 are alkyl, saturated or unsaturated, linear or branched, cyclic or acyclic from 1 to 22 carbons.

CARBONDISULFIDE DERIVED ZWITTERIONS

BACKGROUND

Field of the Invention

The present invention relates generally to the field of amines and more particularly to a classes of amino zwitterions.

Description of the Problem Solved by the Invention

Amines are extremely useful compounds in the buffering of biological systems. Each class of amine has various limitations which require choosing an amine based on multiple factors to select the best amine. For example, pH buffering range is typically most important, but issues of chelation, pH range stability, and solubility also come into play. Typically, a suboptimal buffer will result in yields that are well below the potential yield. The present invention improves the yields in fermentation and purification, and improves shelf stability of proteins and amino acids.

SUMMARY OF THE INVENTION

The present invention relates to amines and amine derivatives that improve the buffering range, and/or reduce the chelation and other negative interactions of the buffer and the system to be buffered. The reaction of amines or polyamines with various molecules to form amine derivatives and polyamines and derivatives with differing pKa's extend the buffering range; derivatives that result in polyamines that have the same pKa yield a greater buffering capacity. Derivatives that result in zwitterionic buffers improve yield by allowing a greater range of stability and reduced conductivity.

DESCRIPTION OF THE FIGURES

Attention is now directed to the following figures that describe embodiments of the present invention:

FIG. 11 shows the synthesis of dithiocarbamates/xanthates hybrids and xanthates amino compounds from aminoalcohols and amino acid esters.

FIG. 20 shows the N-sulfonic acids of a range of primarily secondary amines.

FIGS. 23 and 24 show the synthesis of a series of oil soluble zwitterions and polyamines.

FIG. 25 shows the synthesis of a series of quaternary ammonium compounds with a wide range of uses.

FIG. 26 shows the synthesis of surfactants useful as emulsifiers and other uses where hydrophilic and hydrophobic species need to come into close contact.

Several drawings and illustrations have been presented to aid in understanding the invention. The scope of the present invention is not limited to what is shown in the figures.

DETAILED DESCRIPTION OF THE INVENTION

Figure 1:
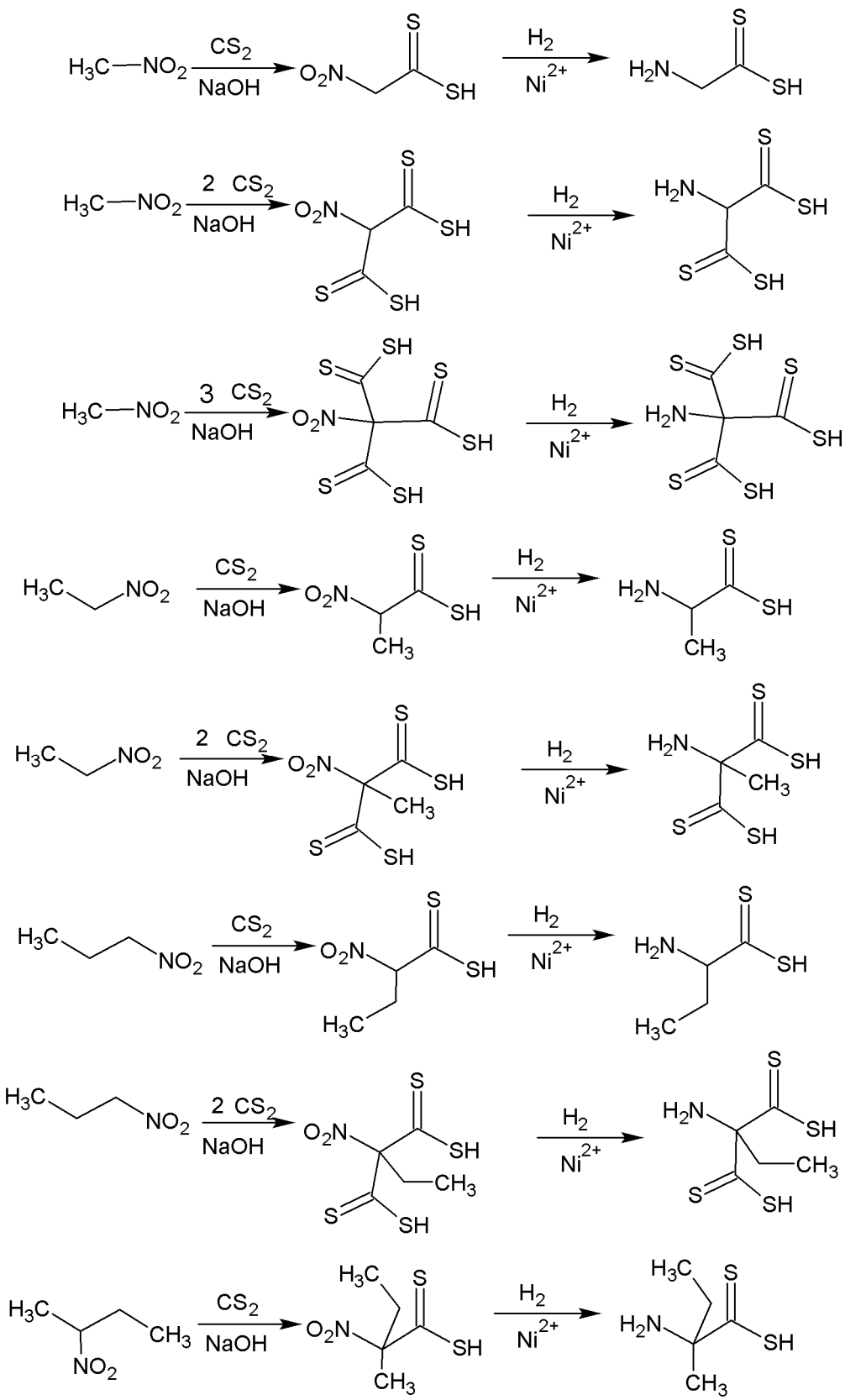
FIG. 1-2 shows the synthesis of zwitterion type buffers from nitroparaffins.
Figure 2:
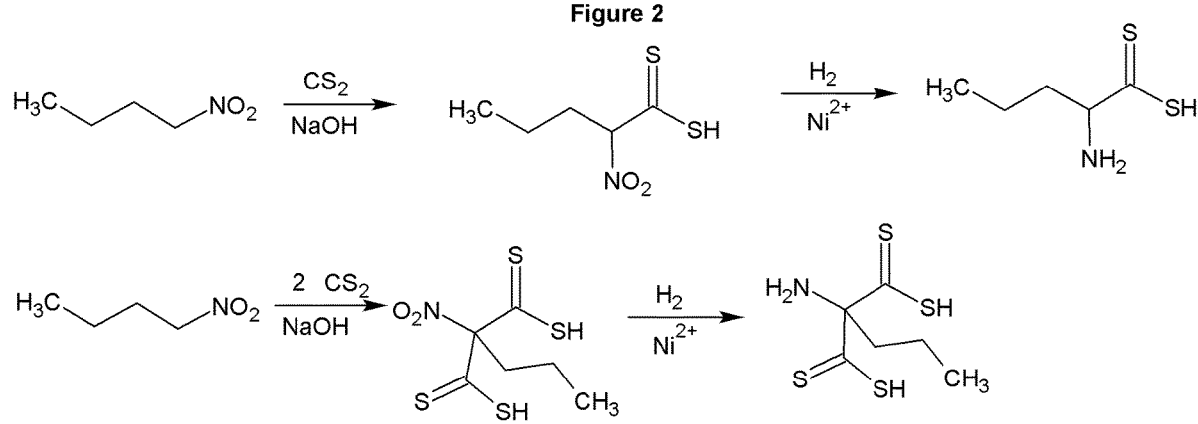
Figure 4:
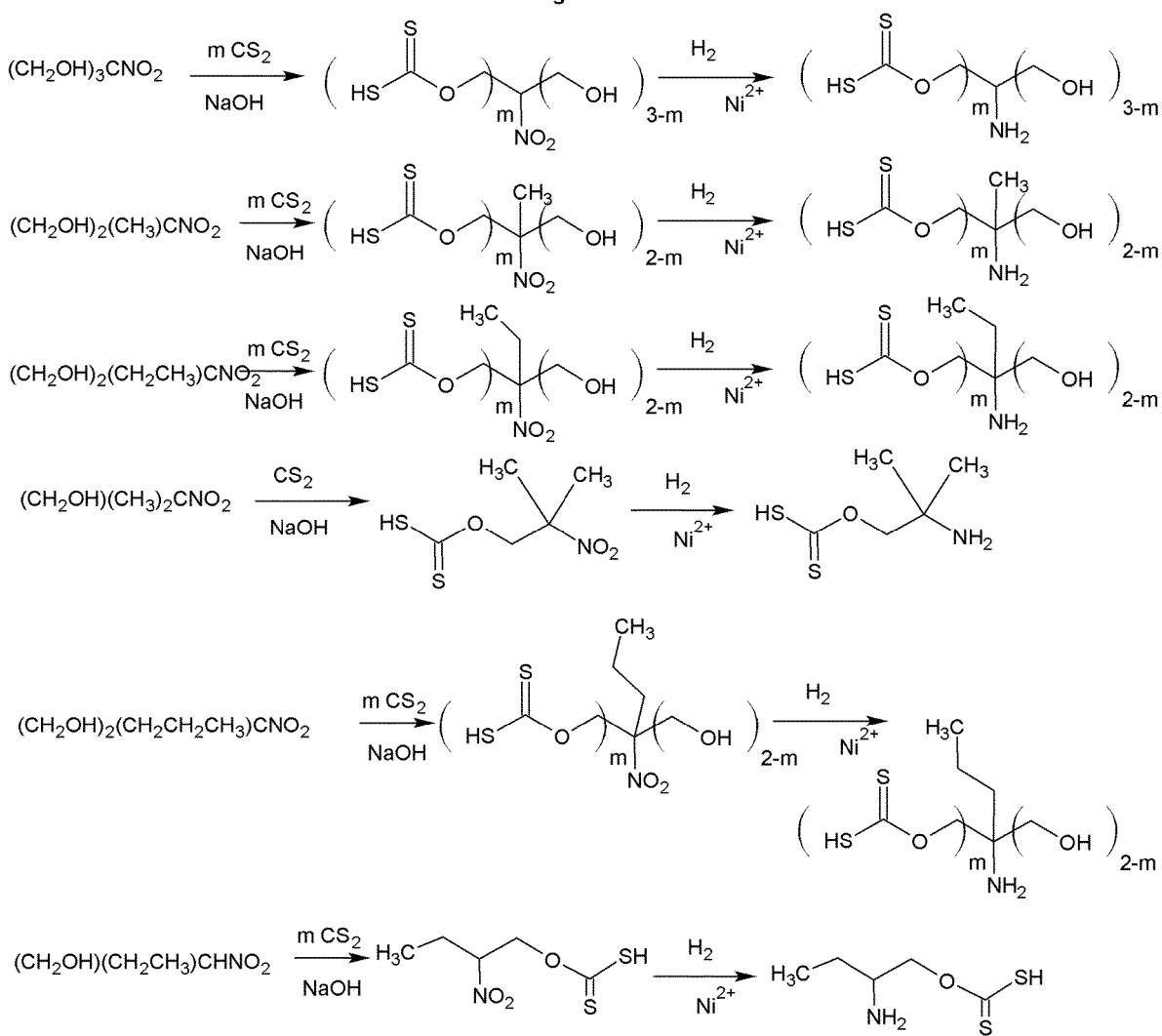
FIG. 4 shows the synthesis of xanthates from nitroparaffins.

The reaction of carbon disulfide with nitroparaffins or nitroalcohols form an intermediate from which xanthate and primary amine functionality can be present in the same molecule through relatively simple, and high yield reactions. FIGS. 1, 2 and 4 depict the route to nitro xanthates, which have utility as cross linking agents and vulcanizing agents and rubber. The nitro functionality improves adhesion of the rubber to the cord in steel belted radial tires and fiber reinforced tire applications as well as other reinforced rubber applications. The nitroxanthates can be utilized as intermediates in the manufacture of primary amine functional xanthates for biological systems, agriculture and antimicrobials as well as many other applications. It should be noted that here, as well as in other embodiments of the invention where a reduction takes place when a xanthate or dithiocarbamate functionality is present, the reduction of the nitro to the amine must be done under relatively mild conditions to limit the co-products of reducing the xanthate functionality. The xanthates and dithiocarbamates have additional functionality in agriculture. The traditional uses such as chelants, and dispersants, are complimented by their use as antifungal, antimicrobial as well as growth regulators as promoters as well as phytocides and insecticides. Often the effects are more pronounced when produced as metal salts, such as zinc, tin, copper or any other transition metal salts.

Figure 3:
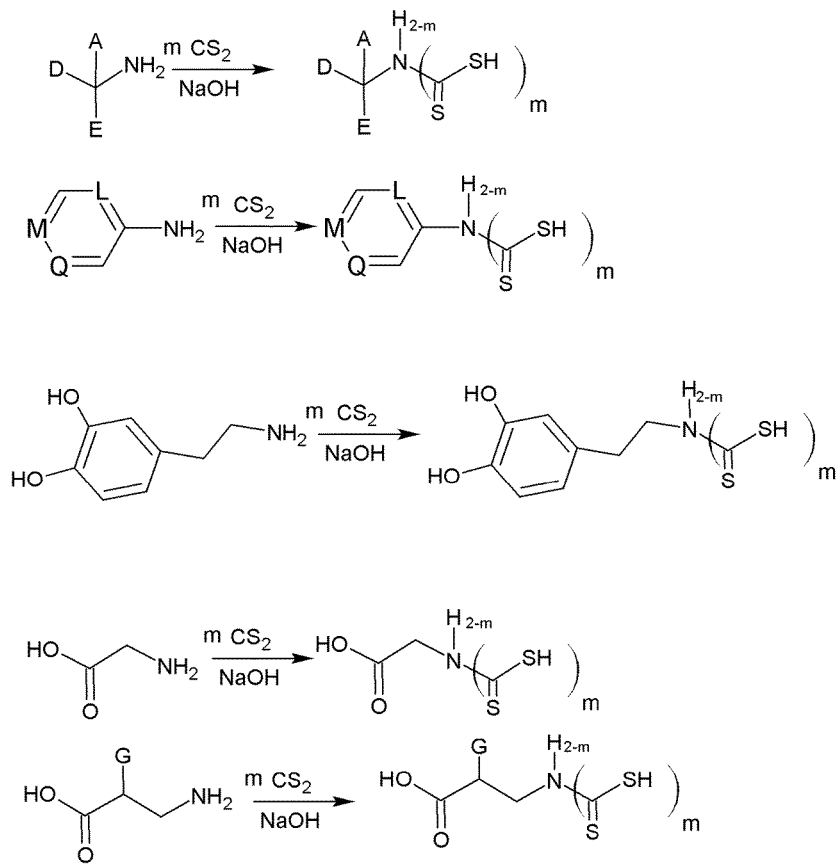
FIG. 3 shows the synthesis of dithiocarbamates from a series of biologically active amines.

FIG. 3 shows the synthesis of dithiocarbamates from a range of biologically interesting amines. The dithiocarbamates of the alaphatic and aminoalcohols are a low cost dispersant, cross linker, with uses in agricultural, antimicrobial, chelant, mining collector and buffer. While the aromatic amine based dithiocarbamates are useful in the above applications, the cost makes them less commercially viable in those applications, however, they show great promise as therapies for diseases of the nervous system, such as multiple sclerosis, Alzheimer's, and Parkinson's diseases. The potential exists for these molecules and their derivatives to be useful therapies as channel blockers as well, which is believed to be the mechanism by which the molecules of the present invention act as an MS therapy. Additionally, the dithiocarbamates are anti-oxidants and have potential as nutritional supplements as well as cancer therapies.

Figure 5:
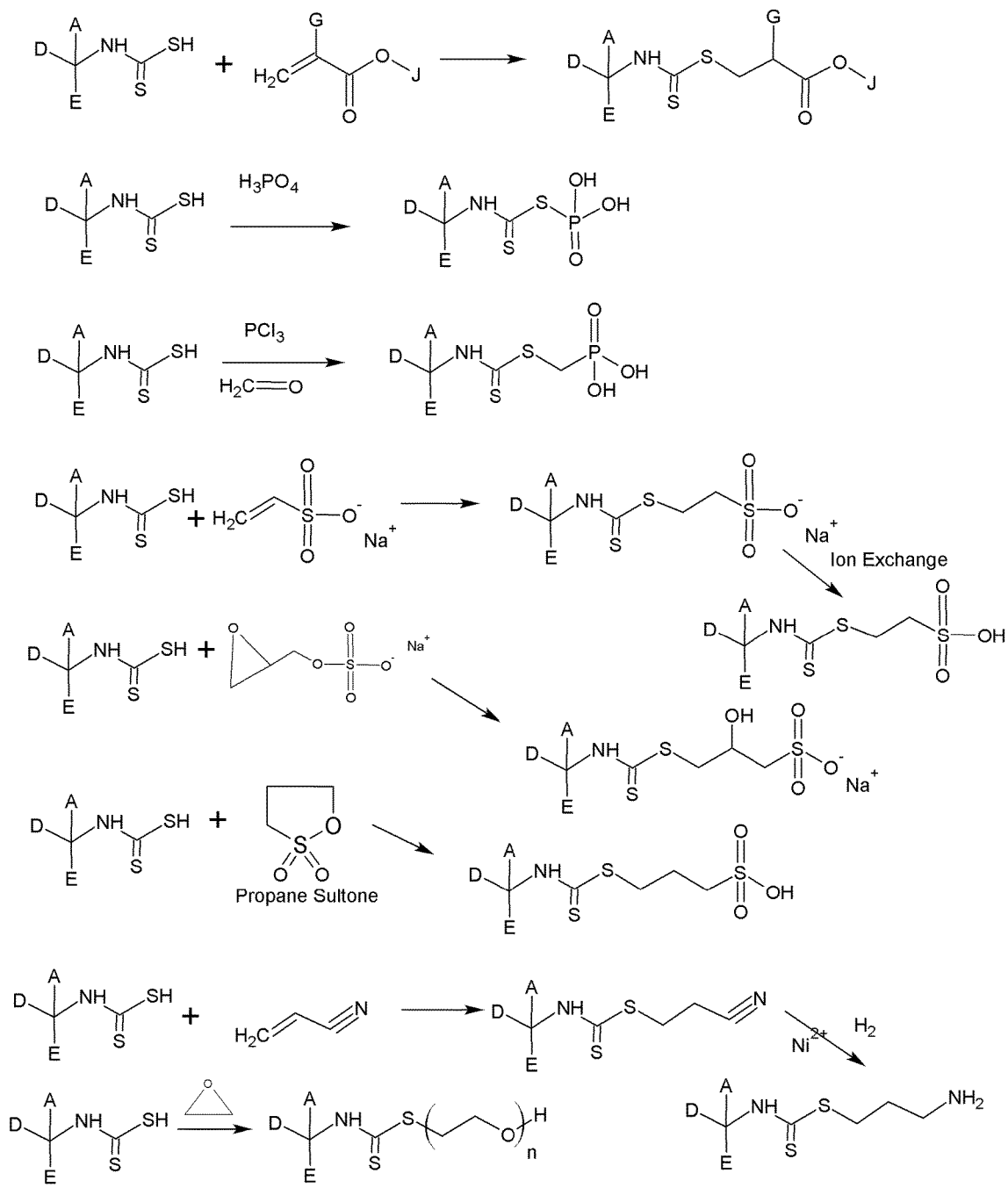
FIG. 5 shows the synthesis of derivatives of dithiocarbamates of biologically active amines.
Figure 6:
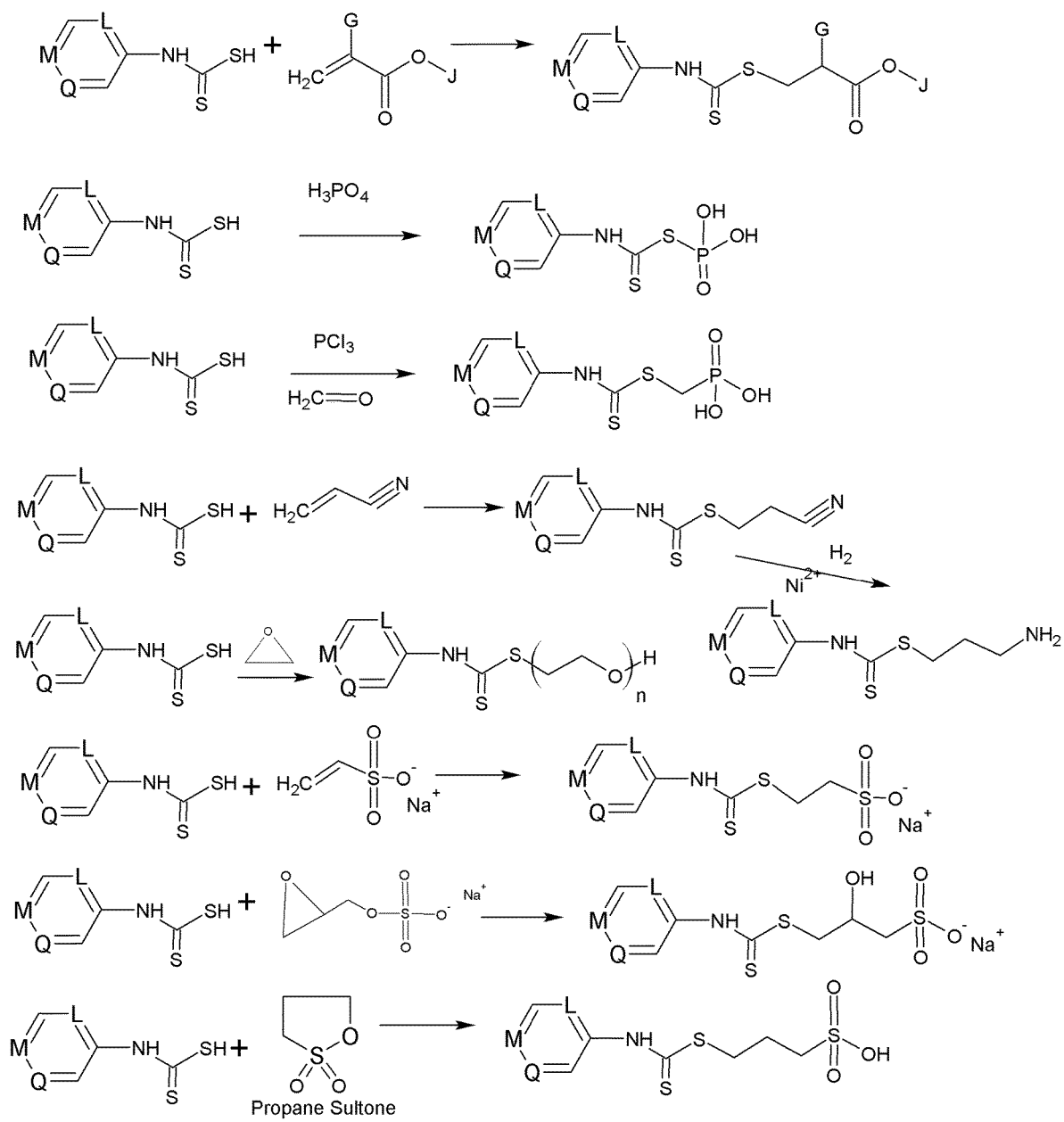
FIG. 6 shows the synthesis of derivatives of aromatic dithiocarbamates.
Figure 7:
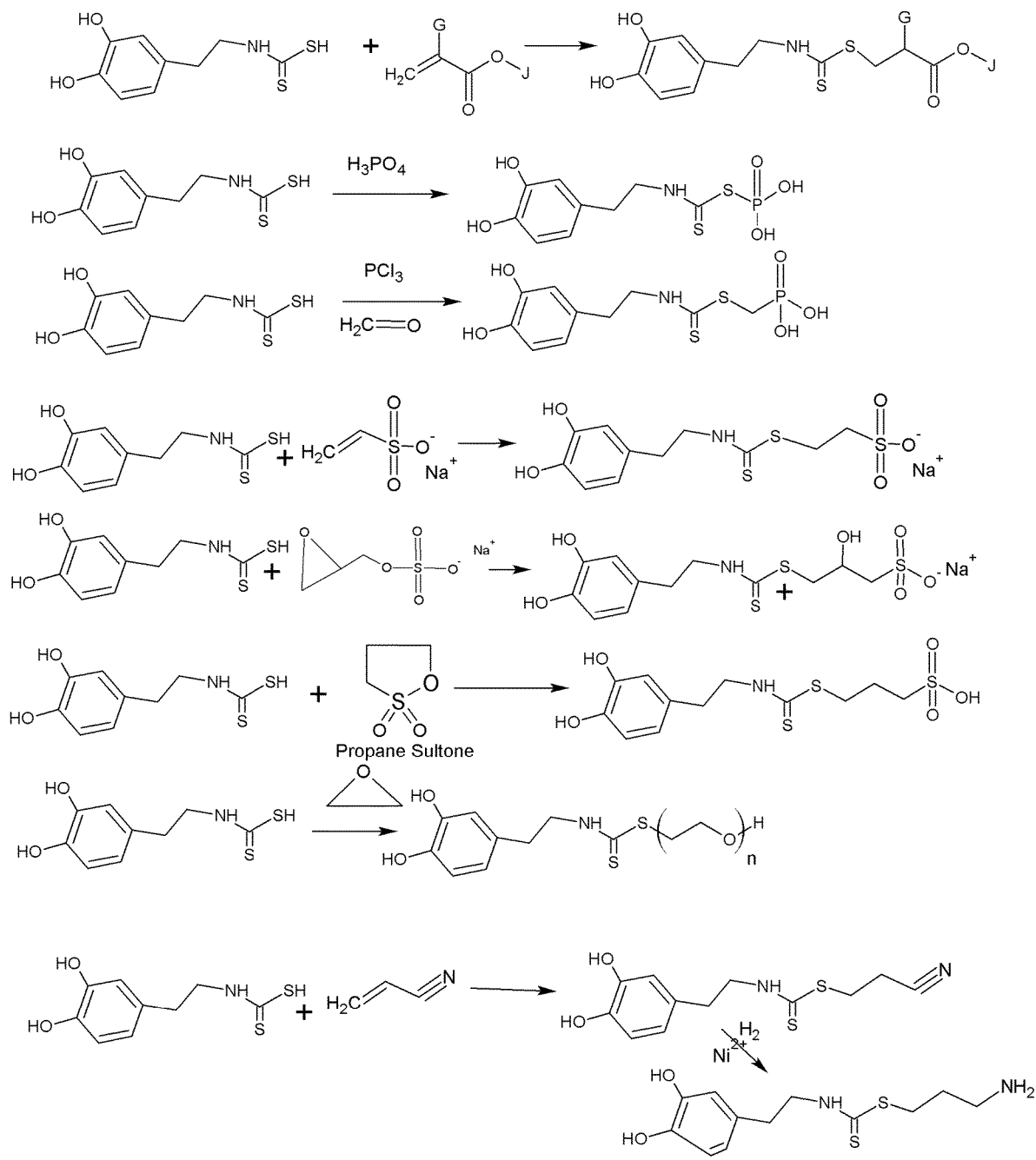
FIG. 7 shows the synthesis of a range of derivatives based on dithiocarbamates of dopamine.
Figure 8:
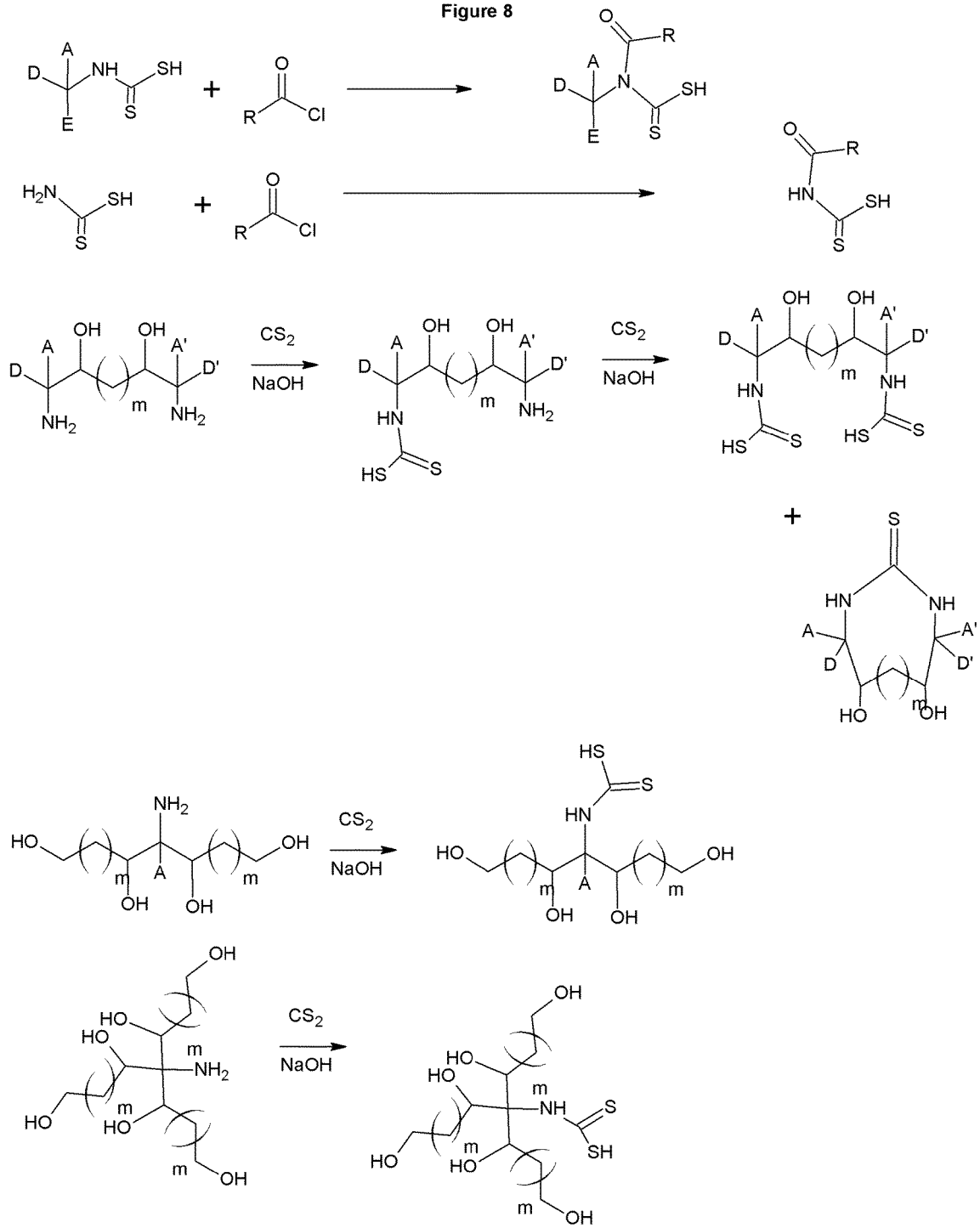
FIG. 8 shows the synthesis of dithiocarbamate dispersants and polyamine dithiocarbamate derivatives.
Figure 9:
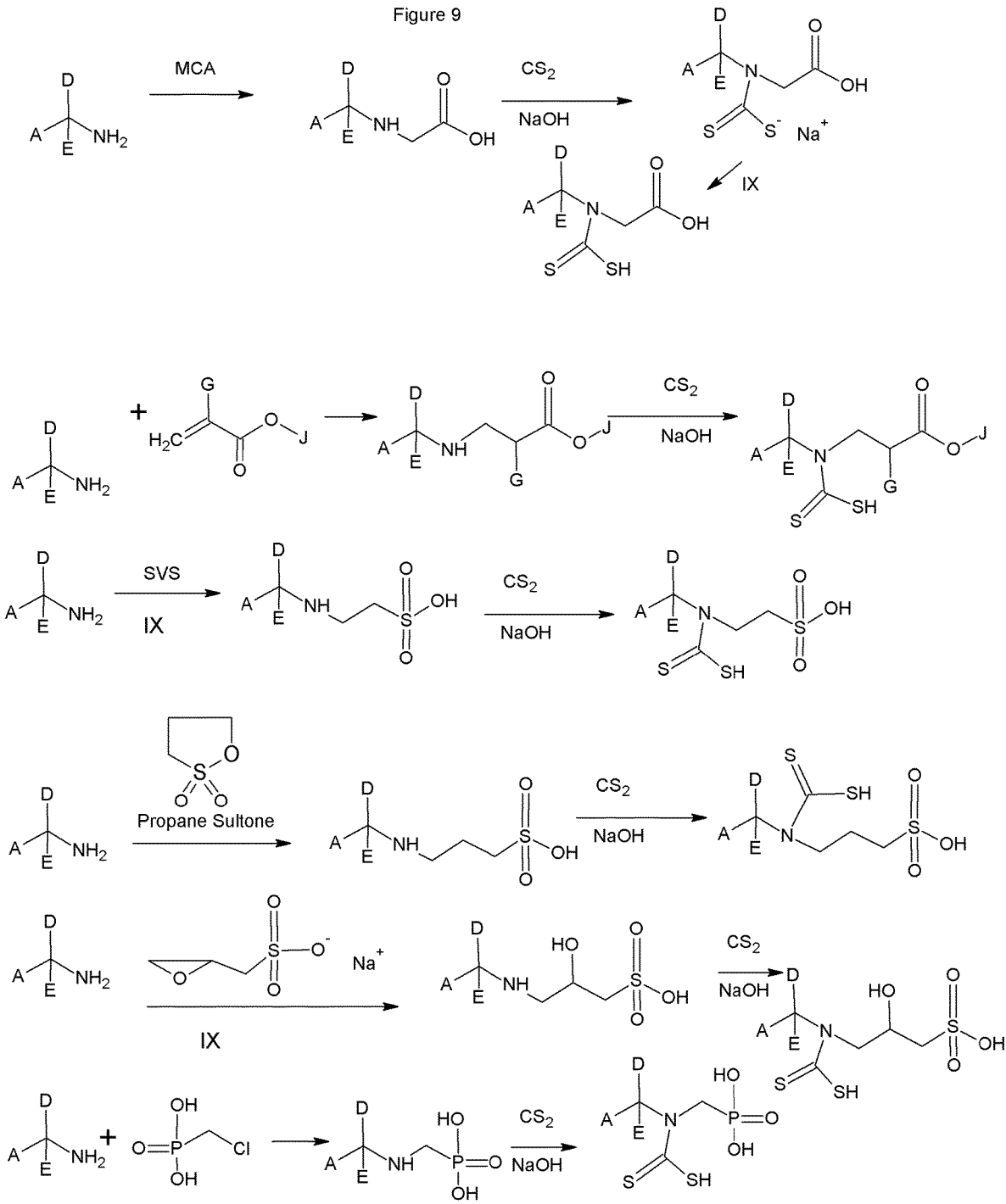
FIG. 9 shows dithiocarbamates from multifunctional secondary amines.
Figure 10:
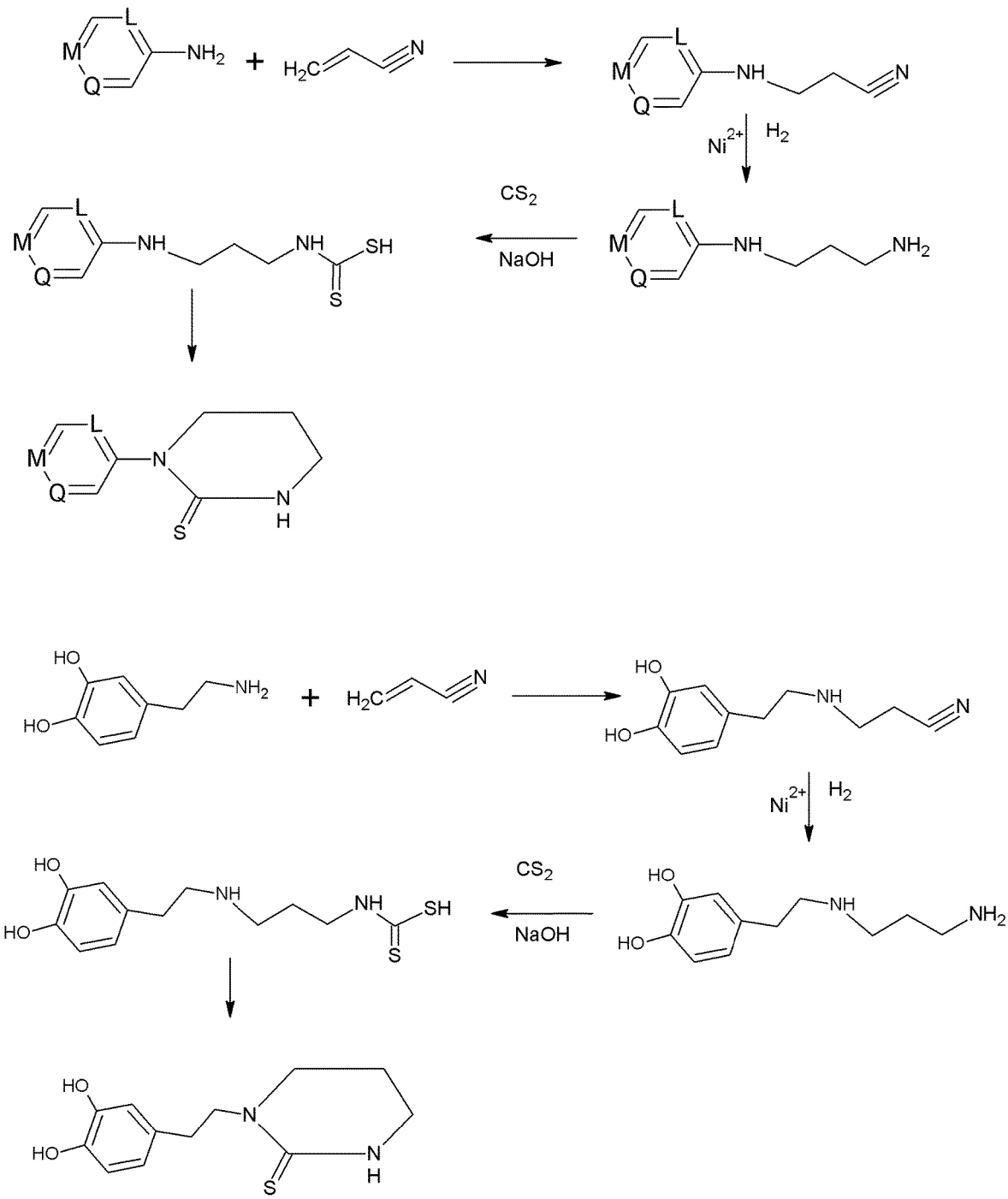
FIG. 10 shows the synthesis of pharmacologically interesting dithiocarbamates.

FIGS. 5, 6 and 7 show the synthesis of several classes of derivatives of the dithiocarbamates previously discussed. Several of the derivatives, particularly the pyridine containing derivatives, are biologically active and potential therapies for mood disorders, multiple sclerosis, Alzheimer's disease, and Parkinson's disease. The carboxcylic acid and ester containing derivatives primarily increase the dispersing capability of the underlying dithiocarbamates, reduce the chelating, or reduce the cost of manufacture. The molecules of FIGS. 6 and 7 that contain aromatic rings and require reduction, must be done under mild conditions, such as iron with turnings or under very mild conditions with sponge metal catalysts at ambient temperatures and pressures of less than 400 psi. The molecules of of FIG. 7 are typically simple one-pot syntheses. FIG. 8 contains several dispersants that are more surfactant in nature, with the higher carbon chain values of R being foam formers. The di-dithiocarbamates from diamines are strong chelants that are of the class bidentate, but tend to undergo ring closure if not kept under basic aqueous conditions. FIG. 9 further expands on these bidentate chelants by introducing other chelant groups. Thus allowing for a wider range of substrates for chelation and dispersion. FIG. 10 shows a family of aminopyridine derived dithiocarbamates as well as a dopamine diamine derived dithiocarbamates all of which are biologically/pharmacologically interesting. Similar to those in FIGS. 6 and 7, the reduction steps must be undertaken under mild conditions to minimize the reduction of the aromatic groups.

Figure 12:
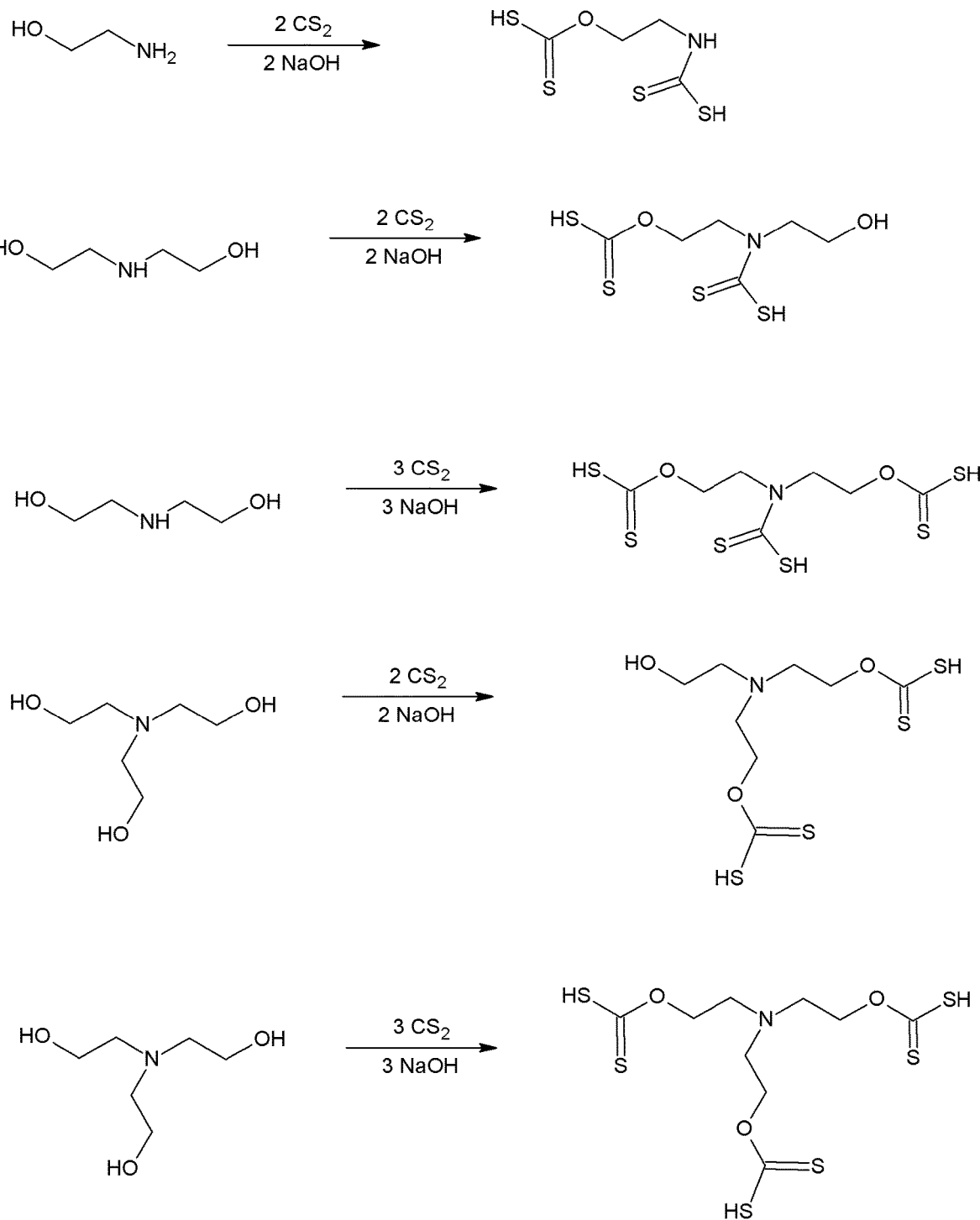
FIG. 12 shows the dithiocarbamates/xanthates based on the typical 3 ethylene amines.

FIG. 11 shows the synthesis of dithiocarbamate/xanthates. Line i gives the example of a dithiocarbamates that possesses an alcohol group. Further exposure to base and $CS_2$ will cause a xanthate to form in place of the alcohol. Line ii carries this forward to include the single step synthesis where 1 or more alcohol groups are present. The A', D', and E' are where any alcohols, if present, have been converted to xanthate groups (—CH2OCS2H), if no alcohol is present for a specific A, D or E, then the prime of the original variable remains unchanged and the original variable. It is understood by one of ordinary skill, that using less than the full amount of $CS_2$ that can be reacted (or base/cation) will result in some alcohol groups not being converted to xanthate groups. This concept is shown in FIG. 12. These products are included as part of the invention. This principle applies to lines iii through vii as well. The same principle applies to the third line on FIG. 8. If alcohol groups are present, then they can be converted to xanthates as shown in FIG. 11. The addition of xanthate groups increases the efficiency of the molecule as a dispersant or mining collector, as well as alter its solubility characteristics. Lines iii through vi produce xanthates of amino acids or amino acid esters. The choice of J allows for a range of solubilities for the free molecule as well as the bound molecule when acting as a chelant, collector or dispersant. Lines v and vi are the result of J being polyethyleneoxide in lines iii and iv. It is understood that this is for illustrative purposes, and that polypropyleneoxide or polybutyleneoxide or other polyalkoxide is part of the invention, as well as their copolymers as J. Line vii shows another way of altering the solubility by substituting a less polar group as R. FIG. 12 shows the dithiocarbamates/xanthates based on the typical 3 ethylene amines.

Figure 13:
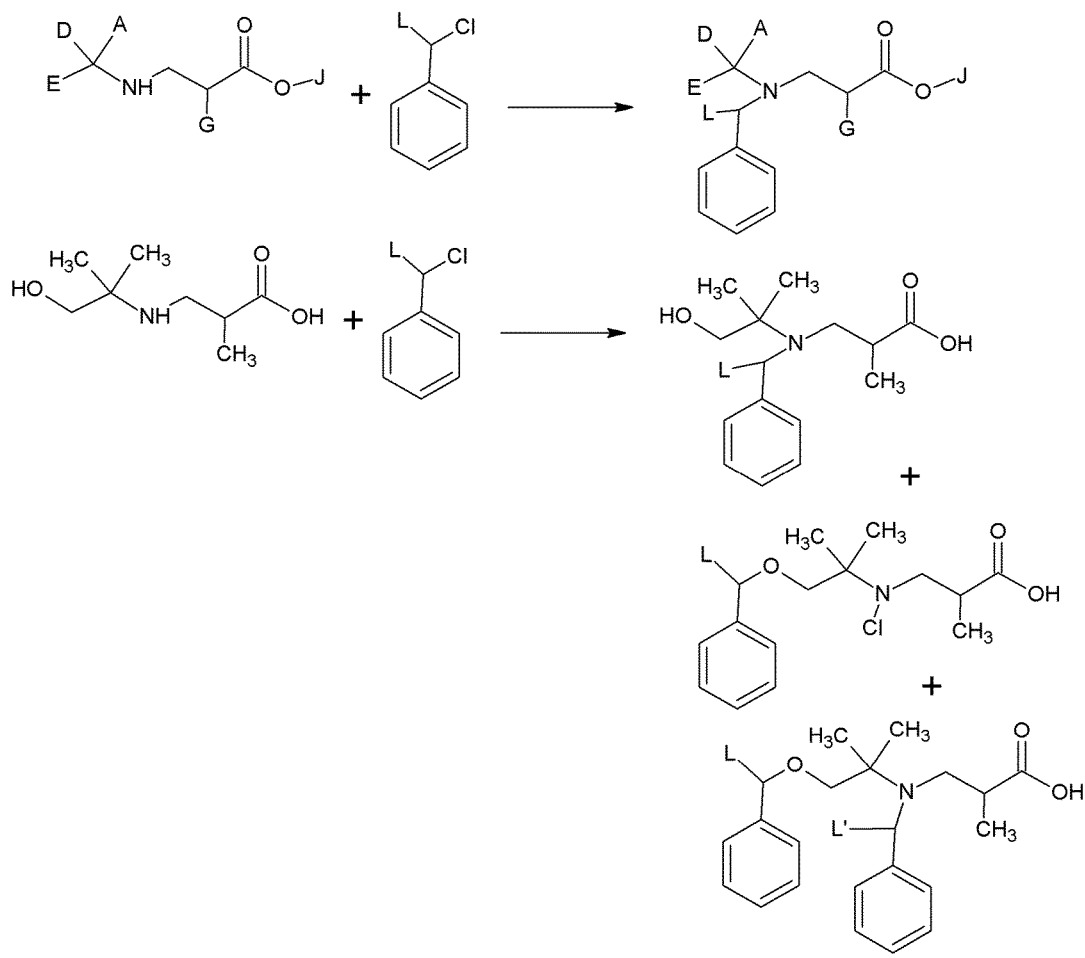
FIG. 13 shows the synthesis of benzyl functional zwitterionics.

FIG. 13 shows the synthesis of benzyl functional zwitterions. The reaction of the benzyl chloride species generates a free chloride ion that will deactivate the amine to further reaction, so much harsher conditions or pH control are necessary to have the reaction go to completion. This becomes a problem once the reaction reaches half-way. In cases where there are hydroxyls present, the reaction will yield a mix of products with some benzyl group addition occurring on the alcohol groups as well as the amine. This is shown in the figure with a single alcohol group present, but is not limited to a single addition. In the cases where more alcohol groups are present, the potential to add to any of them exists leading to greater mix of reaction products. Enough addition of the benzyl chloride containing species can even form a quaternary amine group where two benzyl containing groups add at the amine group.

Figure 14:
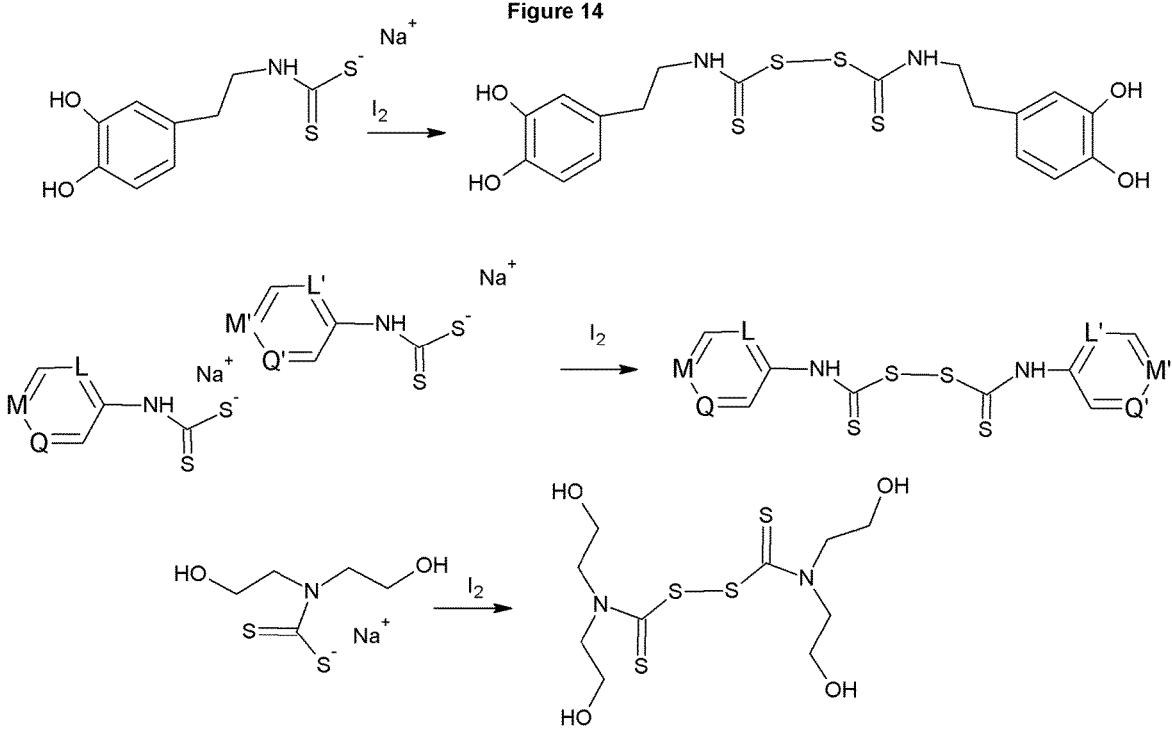
FIG. 14 shows the synthesis of bis dithiocarbamates and bis xanthates
Figure 15:
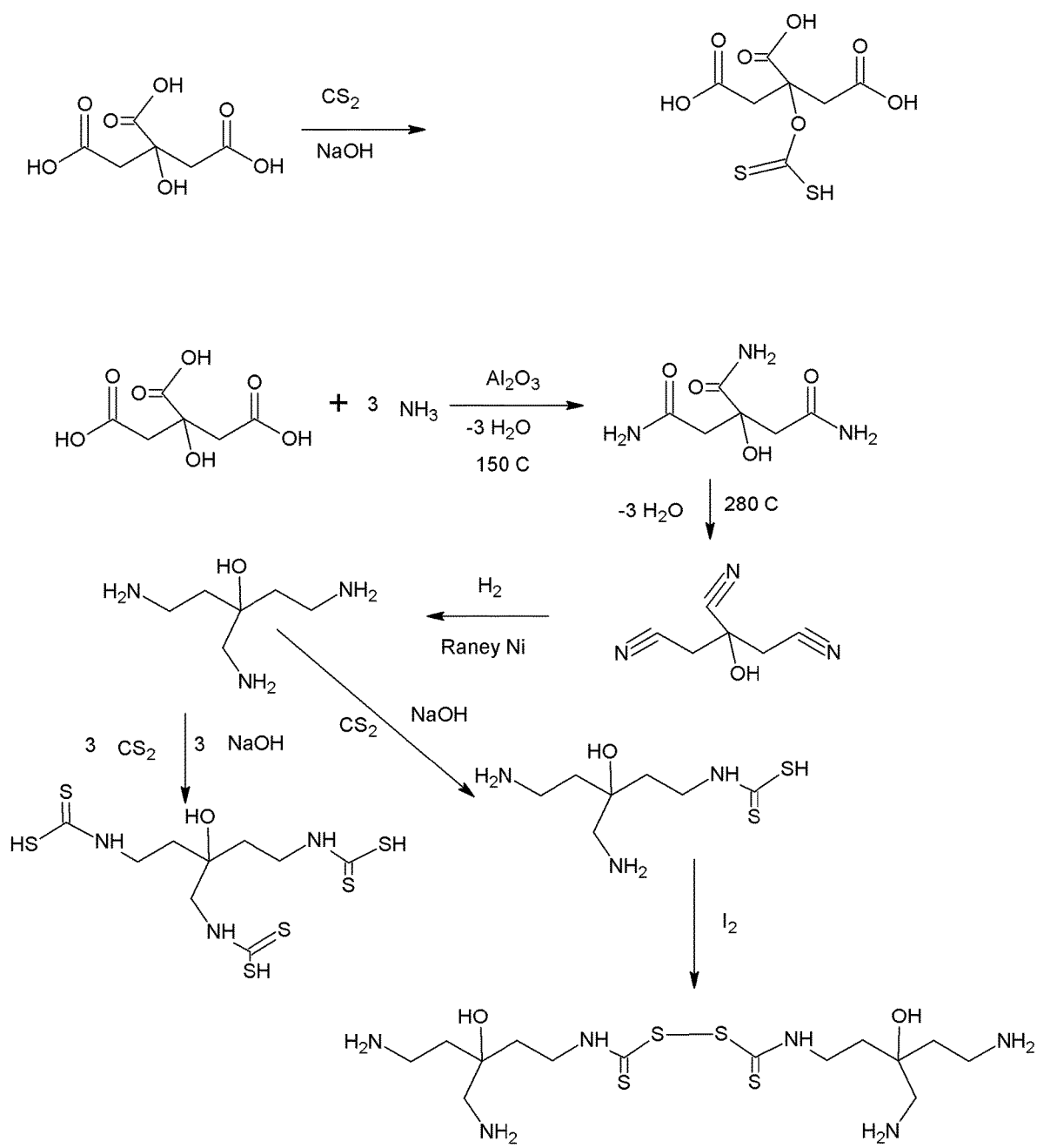
FIG. 15 shows the synthesis of a bis dithiocarbamate based on citric acid
Figure 16:
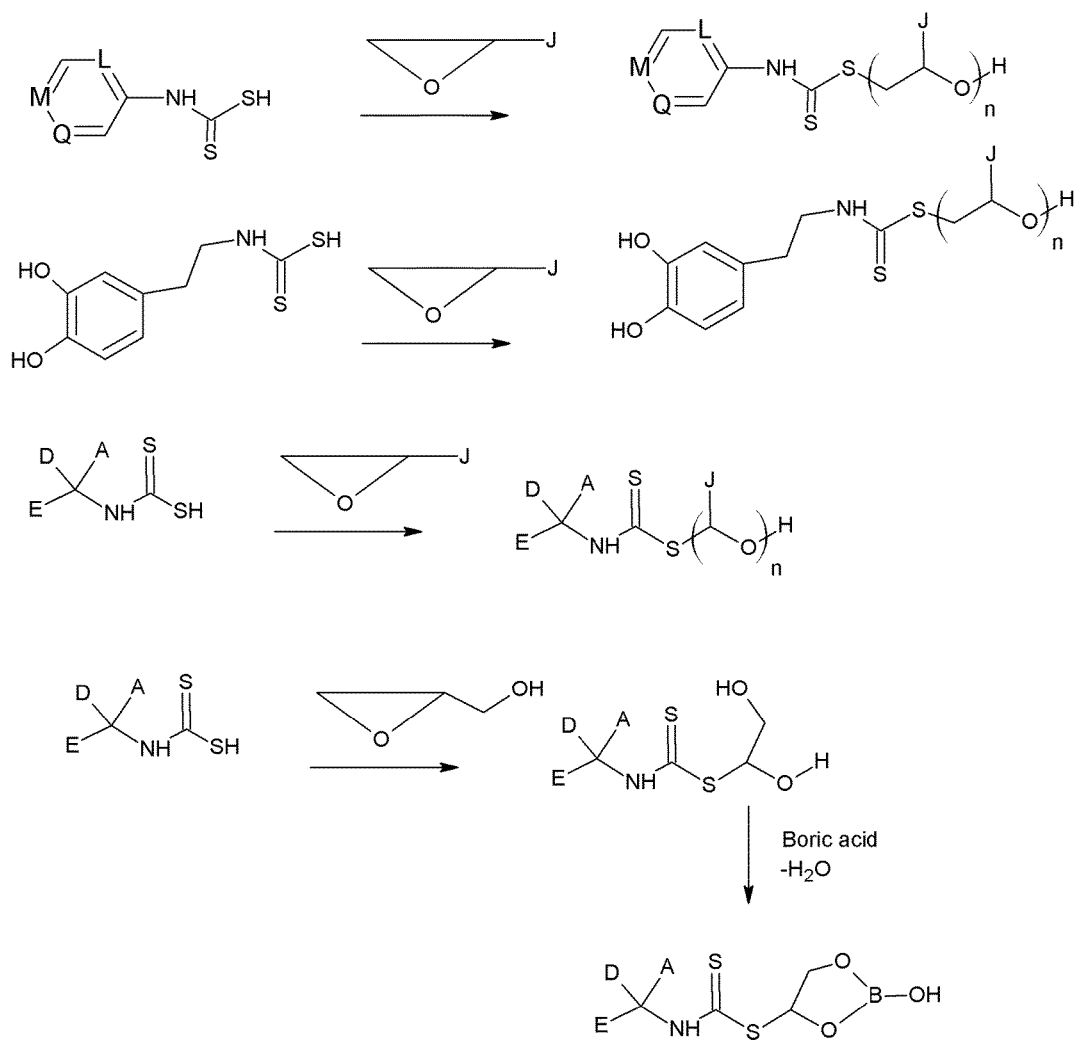
FIG. 16 shows alkoxylates of dithiocarbamates

FIG. 14 shows the synthesis of bis-dithiocarbamates. Bis-dithiocarbamates are useful pharmacology, the most well known bis-dithiocarbamate is disulfiram. FIG. 15 shows an expansion of the bis-dithiocarbamates by using citric acid as the starting material. FIG. 16 shows the alkoxylation of the dithiocarbamates previously taught. While the Figure focuses primarily on the addition to the sulfur of the dithiocarbamates group, more aggressive reaction conditions and additional alkoxylating agents will lead to a mixture of reaction products that include alkoxylation and polyalkoxylation at not just the sulfur, but at the secondary amine group, and any alcohols present. In the case where glycidol is used as an alkoxylating agent, condensation with boric acid leads to particularly good corrosion inhibitors, anti-wear, and lubrication. The non-boric acid condensed products are useful as anti-wear and lubrication additives in their right.

Figure 17:
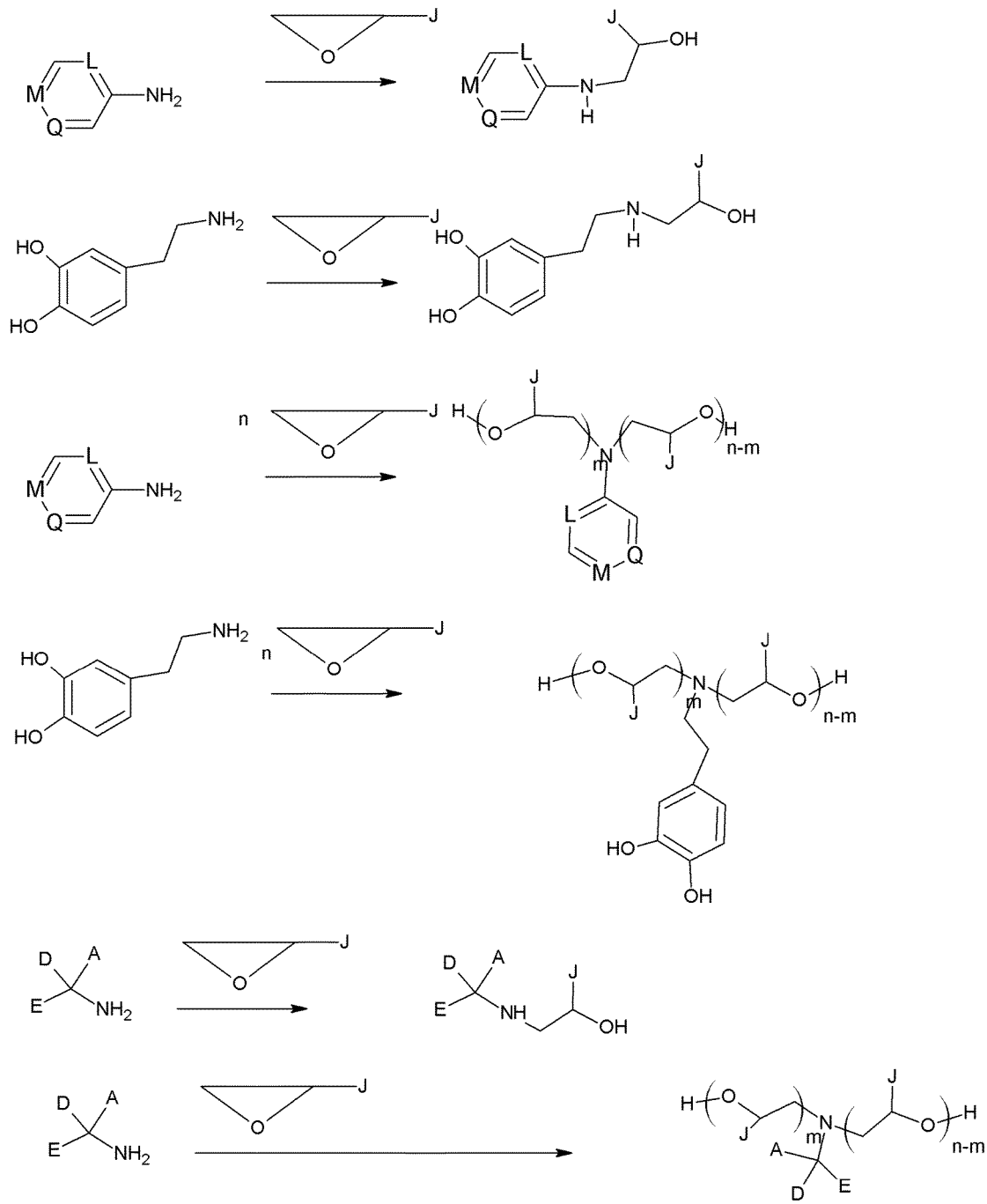
FIG. 17 shows the synthesis of alkoxylates of aminopyridines and dopamine as well as aminoalcohols.

FIG. 17 shows the HLB balancing derivatives of buffers based on aminopyridines and dopamine. These adjustments will adjust the bioavailability of these buffers.

Figure 18:
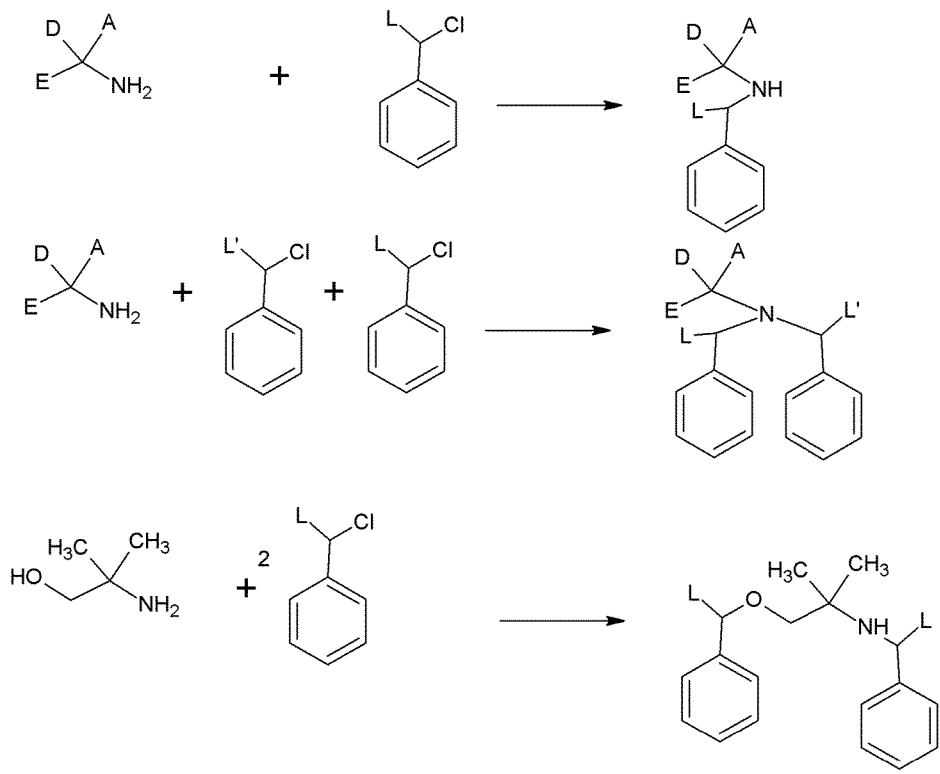
FIG. 18 shows the synthesis of benzyl substituted amines

FIG. 18 shows the synthesis of n-benzyl functional amines. A monosubstituted can be readily made to 50% yield, but pH control during the reaction (addition of base as the reaction proceeds to absorb the chloride ion produced) will allow the reaction to run to completion. N,N disubstituted amines can be made similarly. In the case where alcohols are present in the A, D, or E group, the benzyl containing group will also react on the alcohol group as shown in in the example. It is understood that additional alcohol groups are also subject to substitution if present and sufficient benzyl containing halide is present. Typically, a mixture species with amine and alcohol substitution will be produced when alcohols and amines are present. The case of one alcohol and one amine, with 2 moles of the benzyl containing halide is shown with the dominant product.

Figure 19:
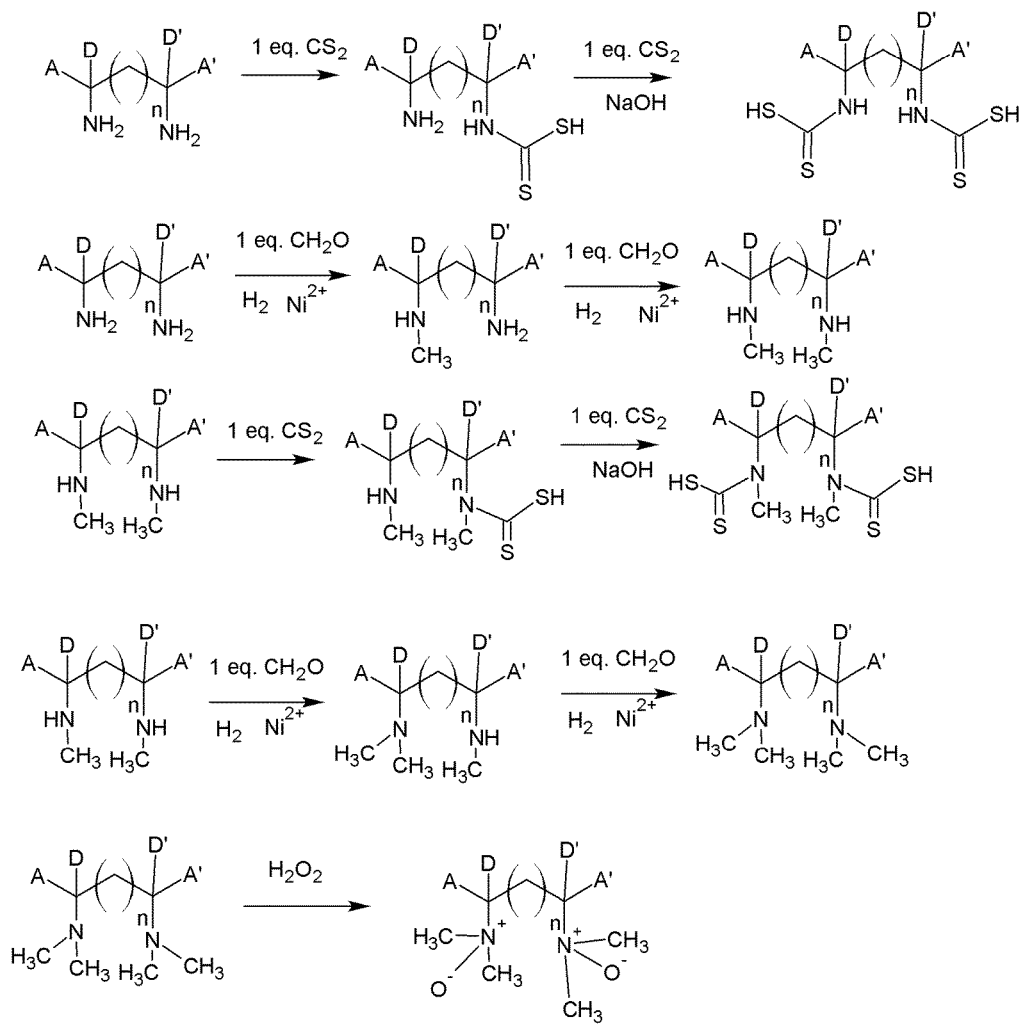
FIG. 19 shows the synthesis of bis-dithiocarbamates and amine oxides

FIG. 19 shows the synthesis of bis dithiocarbamates from diamines. The mono dithiocarbamates can be made from a diamine without introducing mineral salts, such as those of sodium or potassium. The methyl mono and dimethyl amines can also be made by reacting the primary amines with formaldehyde, followed by reduction, typically with hydrogen and sponge nickel. FIG. 20 shows the N-sulfonic acids of secondary amines, as well as the reaction of n-methyl compounds with monochloric acetic acid (MCA), sodium vinyl sulfonate (SVS), propane sultone. It is understood that higher sultones will react in an analogous fashion and are considered part of the invention. Alkoxylation of the n-methyl amines is also taught. The polyoxyethylene derivatives may be mixtures, for example the n-methyl amine may be ethoxylated, then propoxylated to form a block polymer chain off the nitrogen, these block and heteropolymer derivatives are within the scope of the invention. The synthesis of polyamines is taught via the reaction of acrylonitrile and the reduction with hydrogen over sponge nickel. While the diamine is shown, a triamine and higher homologs can be synthesized through successive acrylonitrile reactions on the terminal amine group followed by reductions. Adding 1 mole of acrylonitrile to a primary amine stepwise leads to linear polyamines. Branching can be introduced by adding 2 moles of acrylonitrile in any or all acrylonitrile additions. The polyamines, including the diamine, may be alkoxylated with any alkoxylating agent, typically ethylene oxide, propylene oxide, or butylene oxide in any combination or amount will lead to polyoxyethylene derivatives of the polyamines and are part of this invention, including the stepwise block polymerization with differing alkoxylating agents including the repeating of and alternating of various alkoxylating agents.

Figure 21:
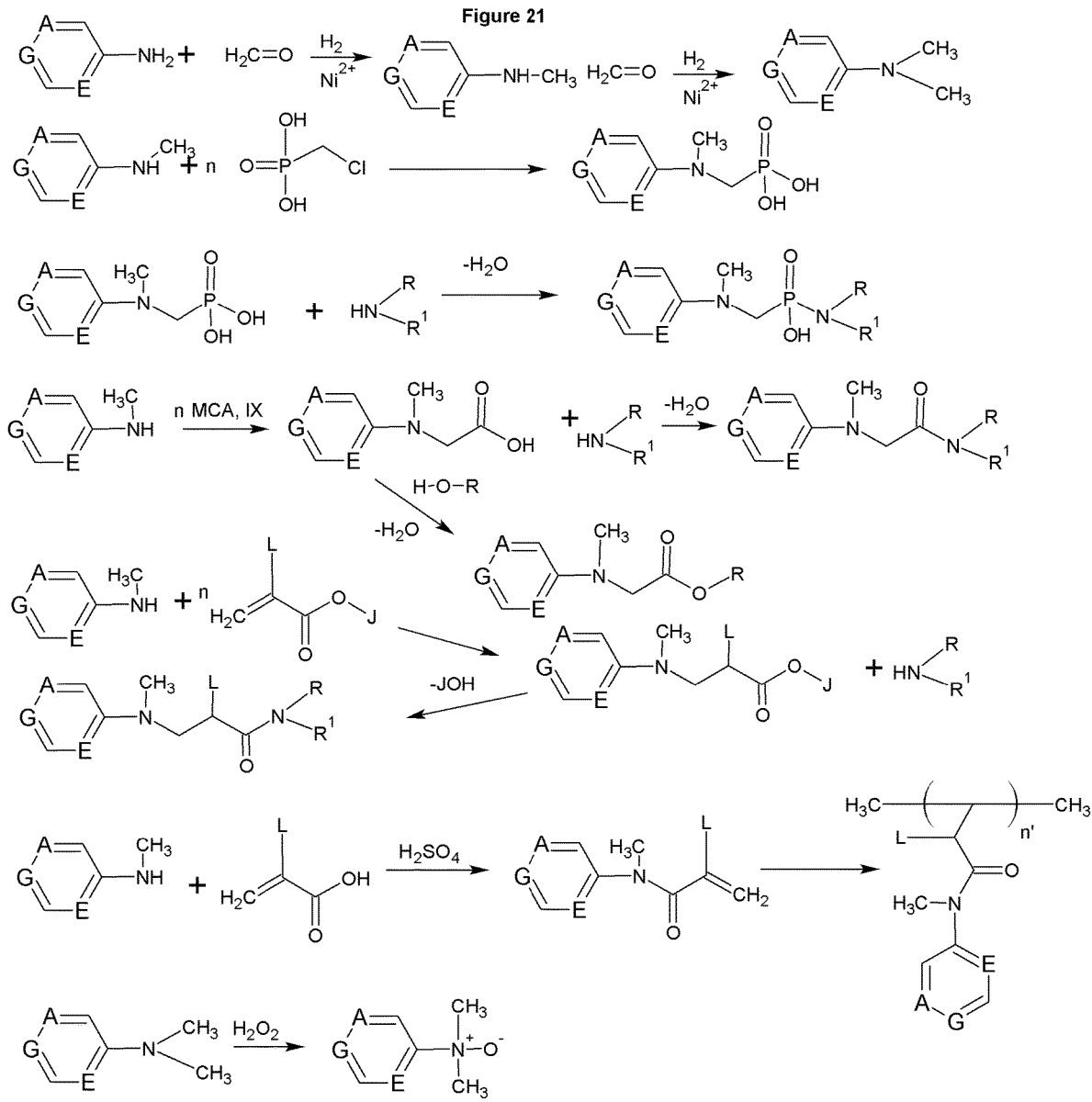
FIGS. 21 and 22 show the synthesis of a range of therapeutic bioactive molecules for treating diseases of the nuerosystem.
Figure 22:
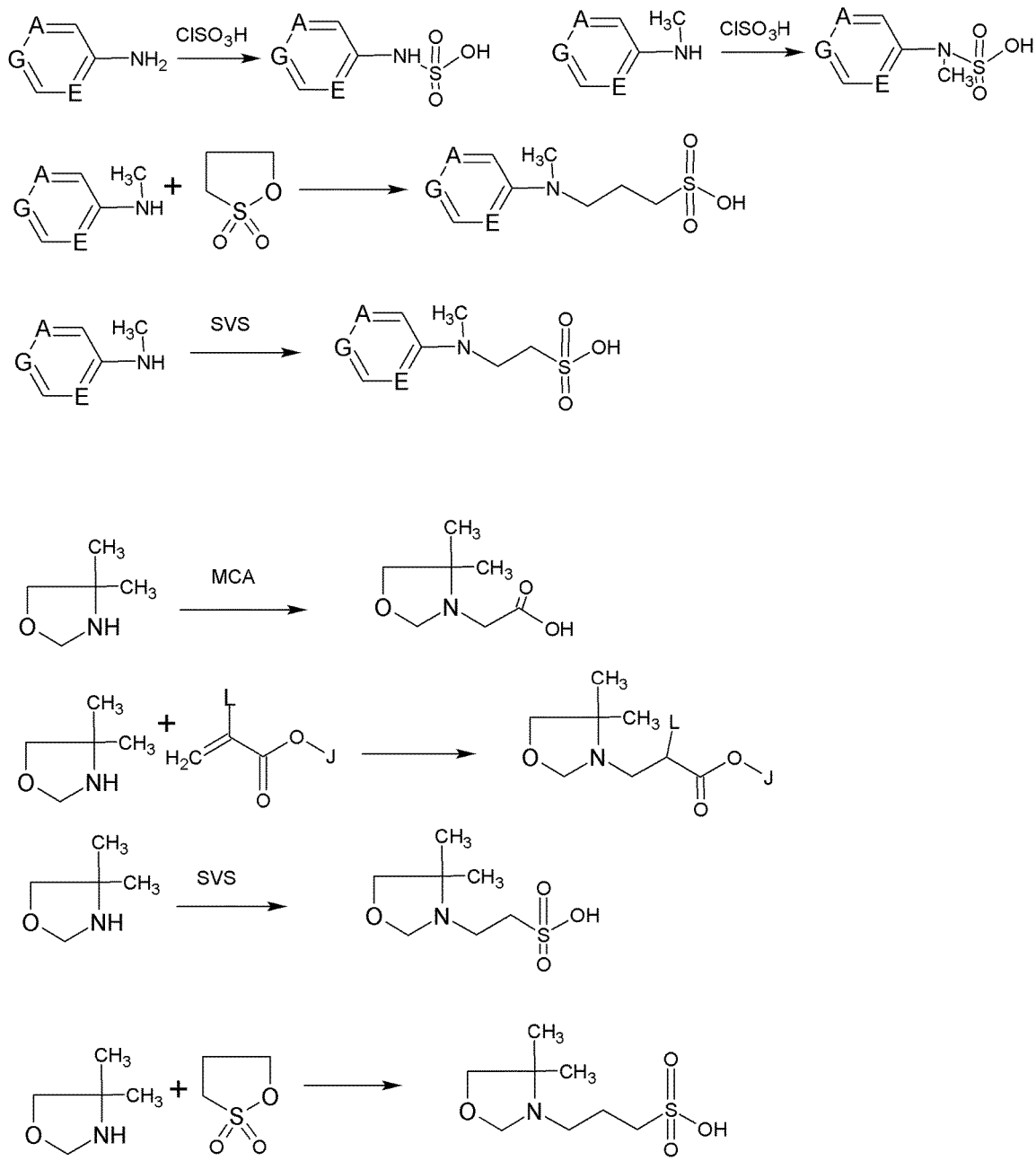

FIGS. 21 and 22 show the synthesis of a range of therapeutic aminopyridine derivatives and intermediates. The primary areas of application are multiple sclerosis, Parkinson's, and Alzheimer's and as monamine oxidase inhibitors. Antimicrobial effects are also observed in the class.

FIGS. 23 and 24 show the synthesis of a range of derivatives of trialkyl primary amines. The largest source of which are the Dow Primene amines (from Dow Chemical). The dithiocarbamates are excellent mining collectors for sulfide ores, such as nickel and copper in flotation recovery as well as antimicrobial, dispersants and pest control. Several zwitterionic species are shown that find utility in surface modification of minerals in floatation mining and in personal care as cleaners. The polyamines are very useful anti-strips in asphalt emulsions. The alkoxylates of both the Primenes and the polyamine derivatives make excellent power improvers in oil pipelines. The amine oxides are excellent emollients and foam builders in personal care, especially shaving cream. While the drawings of the alkoxylation shows a secondary amine resulting, anything over 1 mole of alkoxylating agent will result in a tertiary amine with similar substitutions on both —H positions of the hydrogen. FIG. 25 shows the synthesis of quaternary ammonium compounds. The quaternaries are useful in oilfield as clay modifiers, converting clay, typically bentonite, into a hydrophobic clay for drilling lubrication and for chip removal. The quaternaries are also excellent corrosion inhibitors in oilfield pipelines. The trialkyl quaternaries are excellent fabric softeners and anti-statics. Additionally, the quats and the dithiocarbamates are antimicrobial and are useful in agriculture for fungal and spore control, particularly the ethylbenzyl quats and the dithiocarbamates. The quats are shown as chloride salts and as sulfate salts. This is for illustrative purposes only, any other anion, such as acetate is part of the invention.

FIG. 26 further expands on the alkoxylation of the polyamines of FIG. 24. The most commercially important of the group are the primary amines, which are used primarily as flotation and reverse flotation collectors in iron ore or potash concentration processes. The use of the primary amines of FIG. 24 can be used in the same manner as primary Tallow amine, Commonly known as Crisamine PT, by Crison Chemistry, or isodecyloxypropylamine, commonly known as Tomamine PA-14. The diamines in FIG. 24 are useful as well and used similarly to tallow diamine, commonly known as Crisamine DT, and isodecyloxypropyl-1,3-diaminopropane, commonly known as Tomamine DA-14. The polyamines of FIGS. 24 and 26 are excellent anti-strips in emulsion asphalt formulations. The alkoxylates, are useful as emulsifiers to emulsify the bitumen in emulsion asphalt formulations. The most useful of the alkoxylates are diamine with 3 moles of ethylene oxide, the triamine with 4 moles of ethylene oxide, and the tertamine with 5 moles of ethylene oxide. Further, the partial or total neutralization with acetic acid of the primary amines, polyamines, and their alkoxylates are more water soluble and improve their performance and particularly the handling and application properties. FIG. 26 shows the acetate of the primary amines, the acetates of the polyamines are made in the same fashion and are also part of the invention.

In the case of the asphalt emulsion formulations, the acetic acid evaporates, leaving a water resistant asphalt. The acetate of the primary amine is helpful in mining as a collector in imparting sufficient water solubility for the collector to come in adequate contact with the target mineral. Over neutralization leads to a reduction in collector performance as the reduced hydrophobicity leads to less flotation. A typical neutralization level of between 15 and 50% is most beneficial for the primary and diamines as used as collectors in direct ore flotation or reverse flotation processes. However, any neutralization level can be used.

FIG. 26 also shows the synthesis of amido acid surfactants. The amido acid surfactants are also useful in mining to control hard water ions that interfere with the flotation process. In addition, the amido acid surfactants can function as collectors as well. The amido acid surfactants also make excellent surfactants for personal care products such as shampoo, lotions and facial scrubs where mildness is required. The amido acid surfactants also find utility in oil well drilling for cleaning out the formation and borehole walls.

Figure 27:
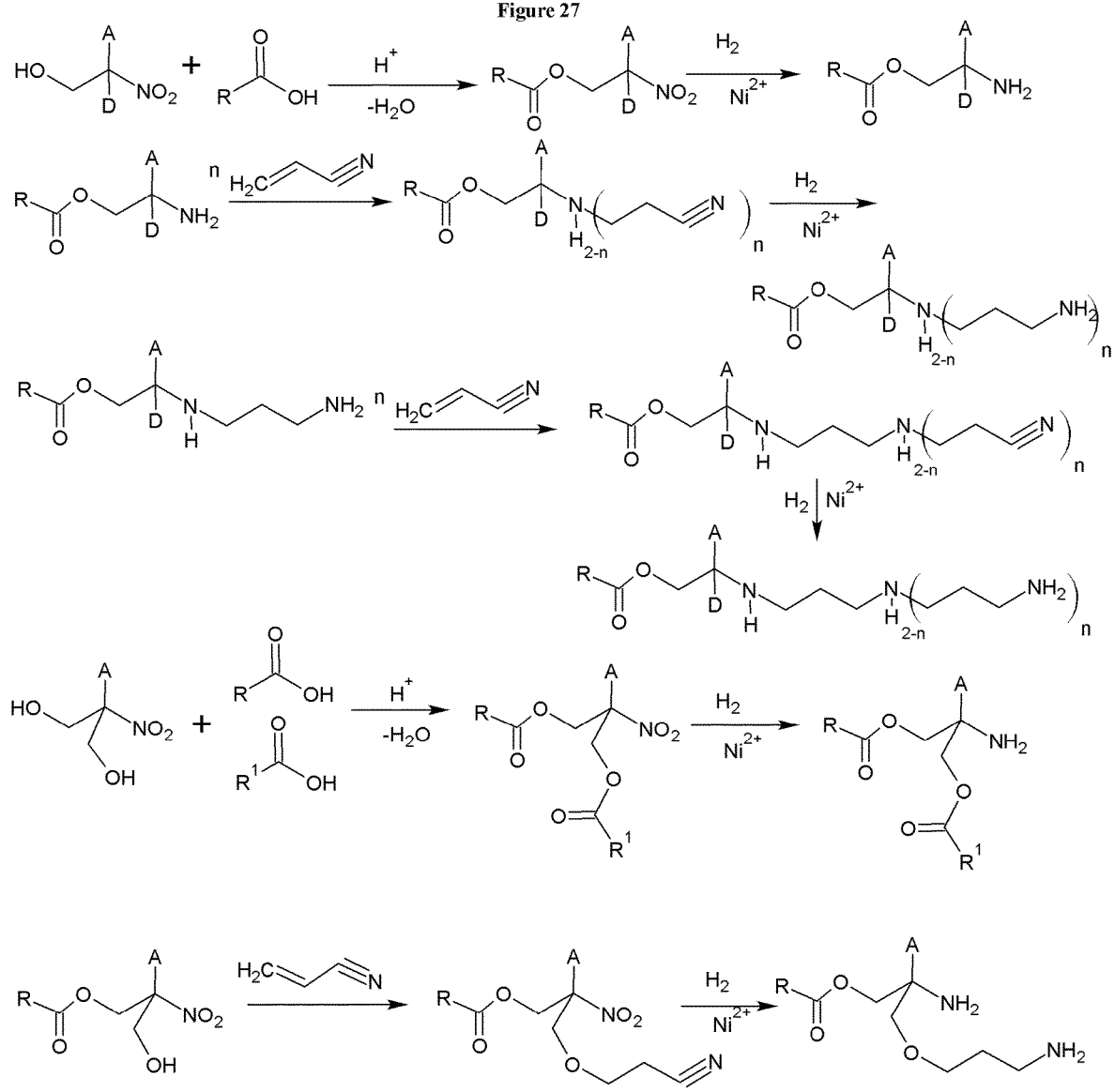
FIG. 27 shows the synthesis of ester amines, ester polyamines

FIG. 27 shows the synthesis of ester amines. The ester amines may be monoalky, dialkyl, or trialkyl. To the extent that an alcohol group is present in the nitro alcohol, it may be esterified, so long as the nitro has not been reduced to the amine. The reduction step needs to take place under milder conditions, where the temperature needs to be controlled. Best results were seen where the temperature was kept below 40 C. Poor results were seen when the temperature exceeded 120 C. Too harsh conditions lead to breakdown of the ester linkage. FIG. 27 also shows the synthesis of polyamines, either through reacting acrylonitrile with any remaining alcohol groups, or through the addition of acrylonitrile to the amine. While the di and triamines are shown, higher analogs can made through subsequent acrylonotrile additions and reductions. Branching can be introduced by adding 2 moles of acrylonitrile per primary amine, or adding sufficient excess as to add to a secondary amine, then reducing the nitrile to the amine. Acrylonitrile based polyamines are typically most useful when reacted with acrylo Useful asphalt emulsifiers can be made by alkoxylating or polyalkoxylating the primary or secondary amine groups, similar to as shown in FIG. 26, as well as any of the alcohol groups. Most common alkoxylating agents are ethylene oxide, propylene oxide, and butylene oxide. However, any other alkoxylating agent may be used, and they are often used in combination to add block copolymer structures to the amine or alcohol group. Further, anti-strips for hot and warm mix asphalt can be made by making amides or polyamides by reacting the amine groups with fatty acid and driving off a mole of water per mole of fatty acid. The ester mono amines are useful as collectors in iron ore purification and potash purification, as well as emulsifiers in asphalt to speed the setting time. The dialkyl and trialkyl mono amines are useful as co-collectors.

Figure 28:
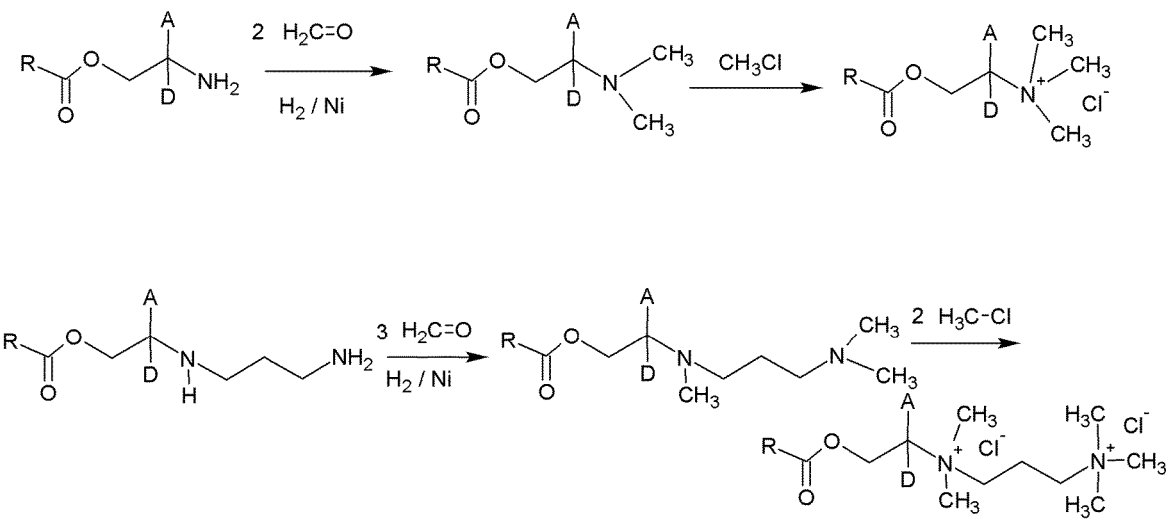
FIG. 28 shows the synthesis of tertiary ester amine quaternaries.

FIG. 28 shows the synthesis of the analogous tertiary amines, as well as their analogous methyl quaternaries. A wider range of quaternaries can also be made by utilizing other quaternizing compounds as shown in FIG. 25. Similarly, the methyl sulfate quats can be made by utilizing dimethyl sulfate instead of methyl chloride.

In the case of the derivatives that are produced as an ionic molecule, the pure zwitterion may be obtained through ion exchange as is routinely carried out on an industrial scale. While the derivatives also show only one dithiocarbamate group, in many cases a second dithiocarbamate group may be obtained as disclosed in the earlier figures. The analogous disubstituted derivative, or mono-substituted analogs are embodiments of the invention. Additionally, where ethylene oxide is shown as a reactant, one skilled in alkoxylations will immediately recognize that ethylene oxide could be substituted with propylene oxide, butylene oxide or any other alkoxylate or any epoxide ring containing compound to generate the analogous product. All of these analogs are within the scope of the present invention. For the derivatives where an amine group results, such as when acrylonitrile is reacted with the nitro xanthates or dithiocarbamates, the amine group can further be derivatized with monochloroacetic acid, allylic acids, sodium vinyl sulfonate, sultones, alkoxylated or phosphonated as shown in my previous patent application Ser. No. 14/079,369. It is further understood by one skilled in the art that higher sultones beyond propane sultone may be substituted and result in the analogous product with additional carbon or carbons between the sulfur and sulfonate group. All of these compounds are also part of the present invention.

Figure 29:
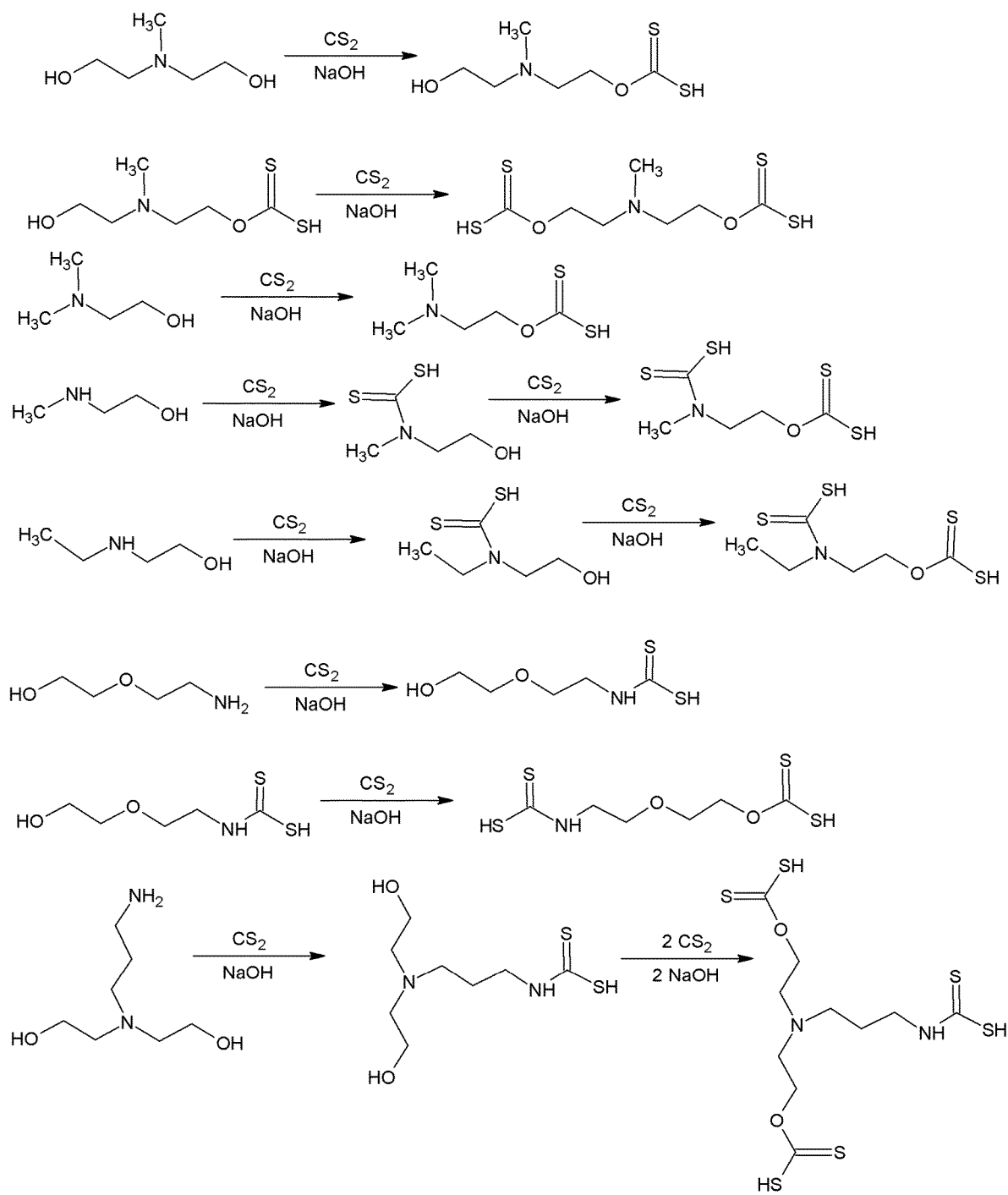
FIG. 29 shows the synthesis of dithiocarbamates and dithiocarbamate hybrids from additional ethanolamines

FIG. 29 expands on FIG. 12 and shows that any amino alcohol can be made into a dithiocarbamate or dithiocarbamate/xanthate hybrid. FIG. 29 simply expands this to explicitly include a wider range of ethanolamines that allows for greater control of selectivity as a mining collector, water solubility for mining depressants and dispersants. In the case of aminopropyldiethanolamine, the dixanthate is shown, but the monoxanthate where a single hydroxyl is retained can be made by reacting with 2 moles of base and 2 moles of carbon disulfide.

Figure 30:
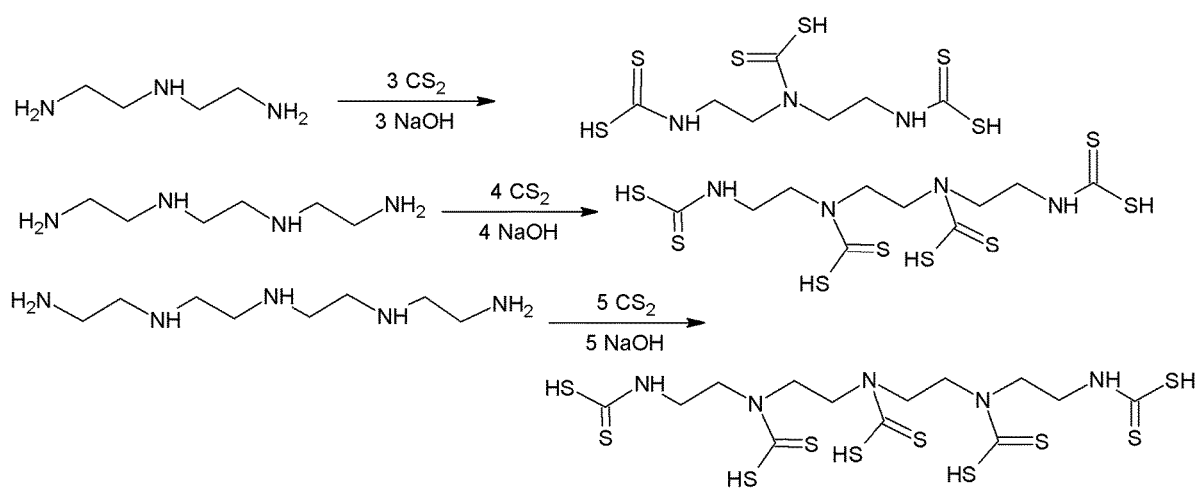
FIG. 30 shows the synthesis of dithiocarbamates from ethylene amines
Figure 31:
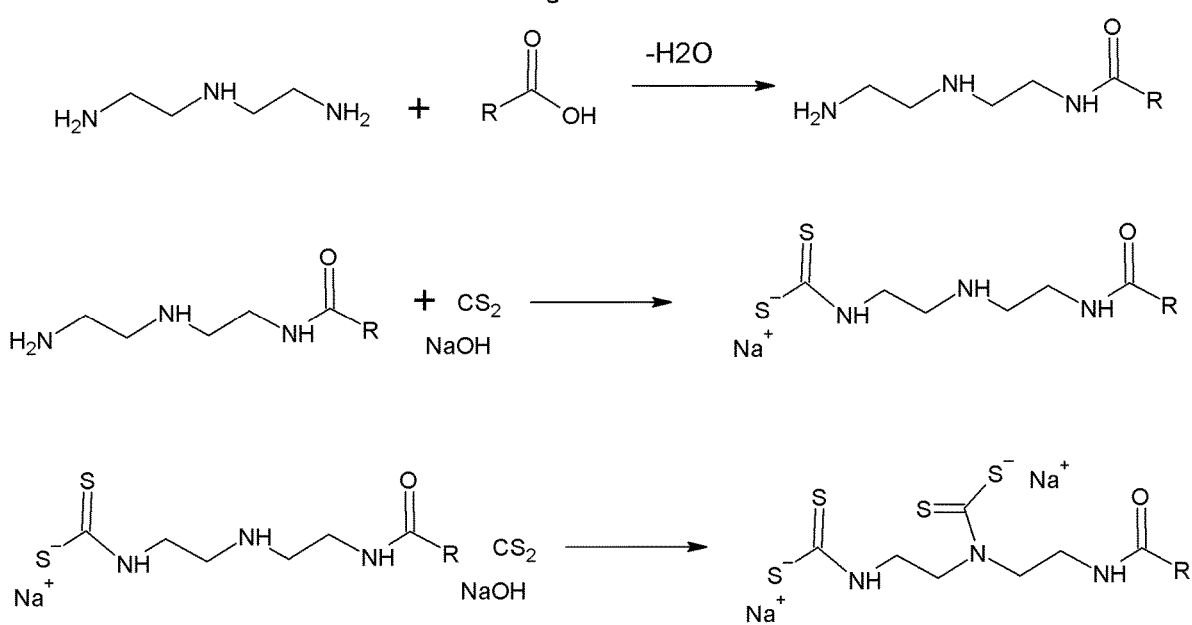
FIG. 31 shows the synthesis of amido dithiocarbamates.
Figure 32:
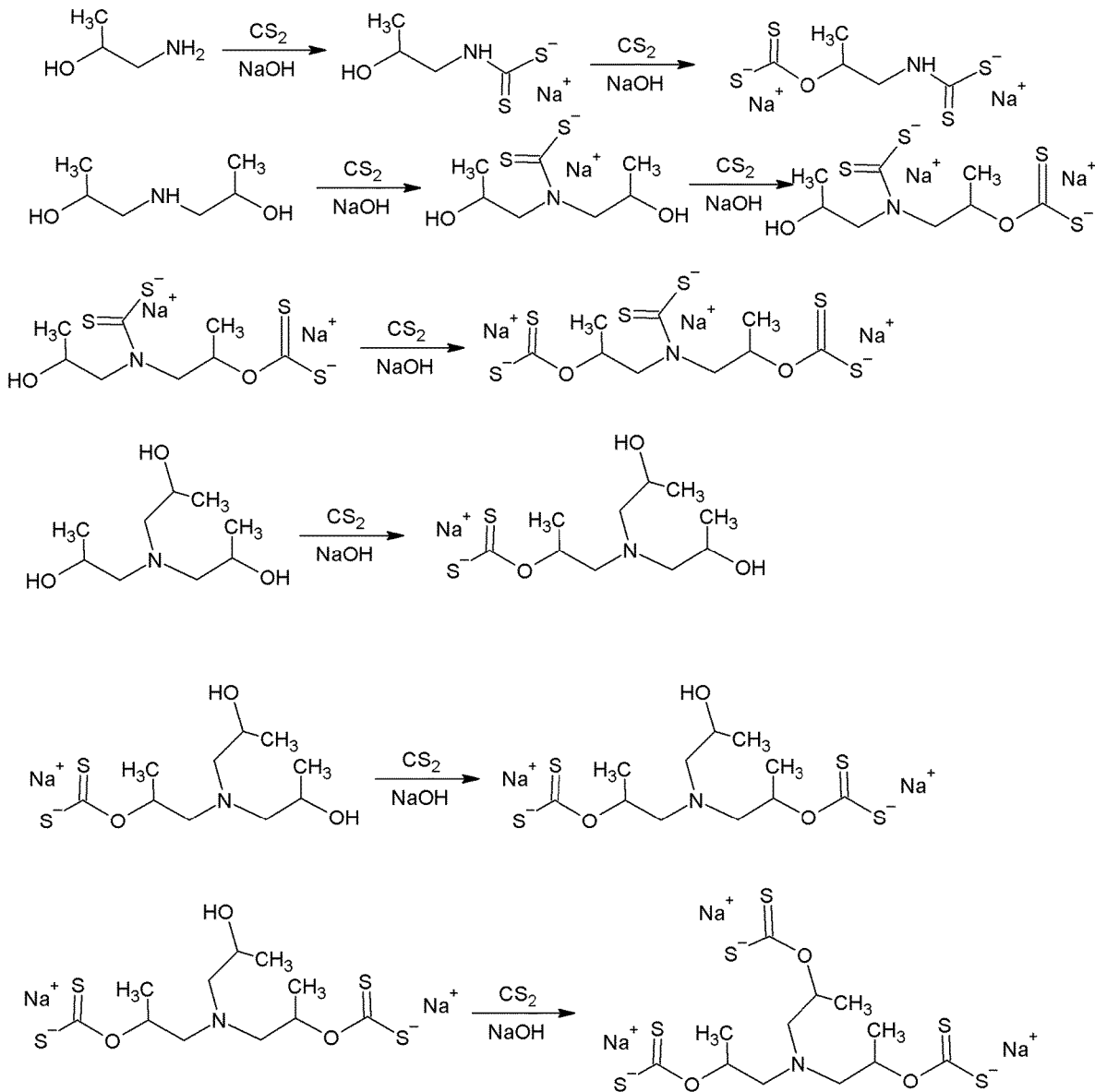
FIG. 32 shows the synthesis of a further range of dithiocarbamate hybrids.

FIG. 30 teaches the synthesis of very strong mining collectors from ethylene amines. Amines groups can be retained in the final product by reducing the molar ratio of carbon disulfide and base. The inner secondary amine groups will be less reactive, and therefore the last to react. The primary amine groups on the ends will be the first to react, and a mixture that contains the didithiocarbamate will also be present when reacting more than 2 moles of carbon disulfide. FIG. 31 expands on FIG. 30 to include amidoamines from ethylene amines to add hydrophobicity the the collectors. While FIGS. 29 and 30 explicitly show ethylene amines as starting materials, propylene amines and the higher homologs of both ethylene amines and propylene amines follow the same synthetic routes and the variants will have differing properties that will each have greater utility versus the other variants based on water conditions and ore composition. The molecules resulting from the use of ethylene amines, propylene amines and their homologs are part of the technology taught in this application. FIG. 31 teaches a family of multi-functional sulfide ore collectors with a range of specificity for particular mineral types, enabling greater efficiency in ore concentration.

The xanthates and dithiocarbamates taught here are most stable and most easily made as salts. The salts are most commonly sodium salts due to the cost effectiveness and availability of sodium hydroxide. While not shown as salts in the figures, it is understood that the salts are within the scope of the invention taught here. The free zwitterions or neutral forms are obtainable via ion exchange, and are what are typically shown in the figures. This is shown explicitly in FIG. 9, in the top reaction series. The salts are not generally shown in the figures to make it clear that all salts, are included in the invention, not just sodium salts. Other bases can be utilized to drive the formation of the xanthates and dithiocarbamates. The resulting salts are within the scope of this invention. Of particular note are the use of tertiary amines to drive the xanthate or dithiocarbamate formation. Not only are small, volatile tertiary amines useful, but so are fatty tertiary amines, monoalkyl tertiary amines, such as the ADMA amines by Lonza, di- and trialkyl tertiaryamines, including tertiary ether amines, such as those produced by Air Products, formerly Tomah Products. Also useful are the tertiary amines that result from alkoxylating primary and secondary amines and ether amines, but care has to be taken not to cause addition to the terminal hydroxyl group. This is controlled by adding the alkoxylated amines in a way that there is a very slight excess of carbon disulfide at all times versus the alkoxylated amine and the amine to be converted to the dithiocarbamate. A further embodiment of the invention taught is the use specifically of tertiary amines containing at least one alkyl branch that is from 10 to 14 carbons in making any dithiocarbamates or xanthates, not just the novel dithiocarbamates and xanthates presented here. These amines show antimicrobial activity that can be taken advantage of to produce dithiocarbamates complexes that have synergistic levels of activity. In agriculture, the use of tertiary amines as adjuvents is common. In particular, 15 moles of ethylene oxide or greater added to tallow amine, such as Akzo Nobel's Armeen T25, or the ethoxylated ether amines, such as Tomamine E-17-5 produces dithiocarbamates that are more readily bioavailable to the target organisms. The use of such amines in the production of all dithiocarbamates and xanthates, not just the novel dithiocarbamates and xanthates taught here, produces dithiocarbamates and xanthate complexes that are much more effective and all such complexes are within the scope of the present invention.

The mineral bases such as lime, calcium hydroxide or potassium hydroxide and all others enable the production of the molecules taught, but without sodium. This is particularly important in agricultural applications. The agricultural applications also benefit from the fatty tertiary amines in that they help the dithiocarbamates or xanthates penetrate the target organism that is to be controlled. If desired, the dithiocarbamates can be made with the starting amine as the counter ion. In this case, two molar equivalents of the amine needs to be utilized to one molar equivalent of carbon disulfide during manufacture.

While much of the benefits of these molecules have been recognized in biological systems, the zwitterions and derivatives are also known to be beneficial as dispersants, chelants, cross-linkers, antimicrobials, preservatives of organic systems, and pH buffers in oilfield drilling systems and hydraulic fracturing. Additionally, the molecules of the present invention find utility as collectors in mining and as depressants. Further, in ball milling, the dispersant characteristics improve the characteristics of ore pellets. The zwitterionic molecules of the present invention also find utility in high energy storage systems, such as lithium ion and lithium polymer batteries as a means of improving charge transport and as acting as a salt bridge in other battery applications. These compounds also find application as asphalt antistrip.

Several descriptions and illustrations have been presented to enhance understanding of the present invention. One skilled in the art will know that numerous changes and variations are possible without departing from the spirit of the invention. Each of these changes and variations are within the scope of the present invention.

I claim:

1. The mining collector and its relevant salts of the following structure:

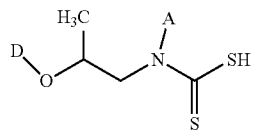

where A is chosen from —H, —CH$_2$CH(CH$_3$)OH, —CH$_2$CH(CH$_3$)OCS$_2$H and D is chosen from —H or —CS$_2$H;
wherein if D=—H, A cannot be —CH2CH(CH3)OH.

2. The mining collector of claim 1 where A=D=—H.

3. The mining collector of claim 1 where A=—H and D=—CS$_2$H.

4. The mining collector of claim 1 where A=—CH$_2$CH(CH$_3$)OH and D=—CS$_2$H.

5. The mining collector of claim 1 where A=—CH$_2$CH(CH$_3$)OCS$_2$H and D=—CS$_2$H.

* * * * *